United States Patent
Hitko et al.

(10) Patent No.: US 11,072,811 B2
(45) Date of Patent: Jul. 27, 2021

(54) SUBSTRATES FOR COVALENT TETHERING OF PROTEINS TO FUNCTIONAL GROUPS OR SOLID SURFACES

(71) Applicant: PROMEGA CORPORATION, Madison, WI (US)

(72) Inventors: Carolyn W. Hitko, Grover Beach, CA (US); Thomas Kirkland, Atascadero, CA (US); Poncho Meisenheimer, San Luis Obispo, CA (US); Rachel Friedman Ohana, Madison, WI (US); Harry Tetsuo Uyeda, Los Osos, CA (US); Ji Zhu, Croton On Hudson, NY (US)

(73) Assignee: PROMEGA CORPORATION, Madison, WI (US)

( * ) Notice: Subject to any disclaimer, the term of this patent is extended or adjusted under 35 U.S.C. 154(b) by 0 days.

(21) Appl. No.: 14/207,959

(22) Filed: Mar. 13, 2014

(65) Prior Publication Data

US 2014/0322738 A1     Oct. 30, 2014

Related U.S. Application Data

(60) Provisional application No. 61/788,257, filed on Mar. 15, 2013.

(51) Int. Cl.
| | | |
|---|---|---|
| C12Q 1/34 | (2006.01) | |
| G01N 33/543 | (2006.01) | |
| C12N 9/14 | (2006.01) | |

(52) U.S. Cl.
CPC ............. *C12Q 1/34* (2013.01); *C12N 9/14* (2013.01); *G01N 33/54353* (2013.01)

(58) Field of Classification Search
CPC ....... C12Q 1/34; C12N 9/14; G01N 33/54353
See application file for complete search history.

(56) References Cited

U.S. PATENT DOCUMENTS

| | | |
|---|---|---|
| 4,810,636 A | 3/1989 | Corey |
| 4,812,409 A | 3/1989 | Babb et al. |
| 6,162,931 A | 12/2000 | Gee et al. |
| 7,238,842 B2 | 7/2007 | Wood et al. |
| 7,416,854 B2 | 8/2008 | Riss et al. |
| 7,425,436 B2 | 9/2008 | Darzins et al. |
| 7,429,472 B2 | 9/2008 | Darzins et al. |
| 7,867,726 B2 | 1/2011 | Wood et al. |
| 7,888,086 B2 | 2/2011 | Darzins et al. |
| 7,906,282 B2 | 3/2011 | Wood et al. |
| 7,935,803 B2 | 5/2011 | Darzins et al. |
| 8,008,006 B2 | 8/2011 | Wood et al. |
| 8,202,700 B2 | 6/2012 | Darzins et al. |
| 8,257,939 B2 | 9/2012 | Wood et al. |
| 8,288,559 B2 | 10/2012 | Corona et al. |
| 8,309,059 B2 | 11/2012 | Corona et al. |
| 8,399,569 B2 | 3/2013 | Murofushi et al. |
| 8,420,367 B2 | 4/2013 | Darzins et al. |
| 8,466,269 B2 | 6/2013 | Darzins et al. |
| 8,476,036 B2 | 7/2013 | Niles et al. |
| 8,557,970 B2 | 10/2013 | Encell et al. |
| 8,669,103 B2 | 3/2014 | Binkowski et al. |
| 8,673,558 B2 | 3/2014 | Fan et al. |
| 8,715,950 B2 | 5/2014 | Riss et al. |
| 8,779,221 B2 | 7/2014 | Darzins et al. |
| 8,895,787 B2 | 11/2014 | Wood et al. |
| 8,921,620 B2 | 12/2014 | Wood et al. |
| 2004/0146987 A1 | 7/2004 | Zdanovsky et al. |
| 2005/0130205 A1 | 6/2005 | Slater et al. |
| 2005/0187147 A1 | 8/2005 | Newman et al. |
| 2006/0127988 A1 | 6/2006 | Wood et al. |
| 2007/0212762 A1 | 9/2007 | Slater et al. |
| 2007/0224620 A1 | 9/2007 | Hartzell et al. |
| 2009/0017482 A1 | 1/2009 | Riss et al. |
| 2009/0263843 A1 | 10/2009 | Anderson et al. |
| 2009/0324621 A1 | 12/2009 | Senter et al. |
| 2010/0062470 A1 | 3/2010 | Corona et al. |
| 2010/0160557 A1 | 6/2010 | Murofushi et al. |
| 2010/0273186 A1 | 10/2010 | Wood et al. |
| 2011/0039257 A1 | 2/2011 | Binkowski et al. |
| 2012/0258470 A1 | 10/2012 | Wood et al. |
| 2012/0330001 A1 | 12/2012 | Darzins et al. |
| 2013/0317207 A1 | 11/2013 | Kirkland et al. |
| 2014/0199712 A1 | 7/2014 | Hitko et al. |

(Continued)

FOREIGN PATENT DOCUMENTS

| | | |
|---|---|---|
| WO | WO 2012/078559 | 6/2012 |
| WO | WO 2014/151282 | 3/2014 |
| WO | WO 2014/093671 | 6/2014 |

OTHER PUBLICATIONS

Dubowchik et al., Bioconjugate Chem., 1995, 6 (4), pp. 427-439.*
STN Registry database entry for CAS RN 1035373-84-2, entry date Jul. 22, 2008, Accessed May 30, 2018.*
Bielski et al., "Strategies for coupling molecular units if subsequent decoupling is required," Chem. Rev. 2013, 113: 2205-2243.
Benink et al., "Direct pH measurements by using subcellular targeting of 5(and 6-) carboxyseminaphthorhodafluor in mammalian cells," BioTechniques 2009, 47: 769-774.
Hong et al., "HaloTag: a novel reporter gene for positron emission tomography," Am J Transl Res 2011, 3: 392-403.
Schaefer et al., "Phenylalanine-containing hydroxamic acids as selective inhibitors of class IIb histone deacetylases (HDACs)," Bioorg Med Chem Lett 2008, 16: 2011-2033.

(Continued)

*Primary Examiner* — Alicia L Otton
(74) *Attorney, Agent, or Firm* — Casimir Jones SC; David W. Staple

(57) ABSTRACT

The present invention provides haloalkane substrates, and linkers for connecting such substrates to functional elements (e.g., tags, labels, surfaces, etc.). Substrates and linkers described herein find use, for example, in labeling, detection, and immobilization of proteins, cells, and molecules. In particular, the linkers provided herein find use within substrates for dehalogenase variants that form covalent bonds with their haloalkane substrates.

9 Claims, 9 Drawing Sheets

(56) References Cited

U.S. PATENT DOCUMENTS

2014/0322794 A1   10/2014   Hitko et al.

OTHER PUBLICATIONS

Wittich et al., "Structure-activity relationships on phenylalanine-containing inhibitors of histone deacetylase: in vitro enzyme inhibition, induction of differentiation, and inhibition of proliferation in Friend leukemic cells," J. Med. Chem. 2002, 45: 3296-3309.
International Search Report and Written Opinion for PCT/US2014/025359 dated Aug. 29, 2014, 24 pages.
Los et al., HaloTag: A Novel Protein Labeling Technology for Cell Imaging and Protein Analysis. ACS Chem Biol. 2008;3:373-382.
Ohana et al., Decipering the Cellular Targets of Bioactive Compounds Using a Chloroalkane Capture Tag. ACS Chem Biol. 2015;10:2316-2324.
Extended European Search Report for EP Patent Application 14769169.8, dated Sep. 5, 2016, 10 pages.

\* cited by examiner

Figure 1
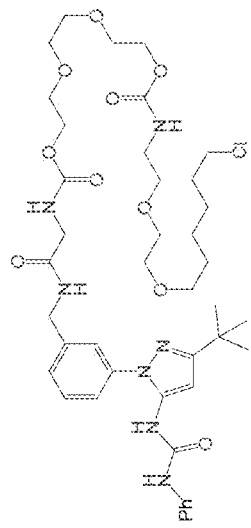
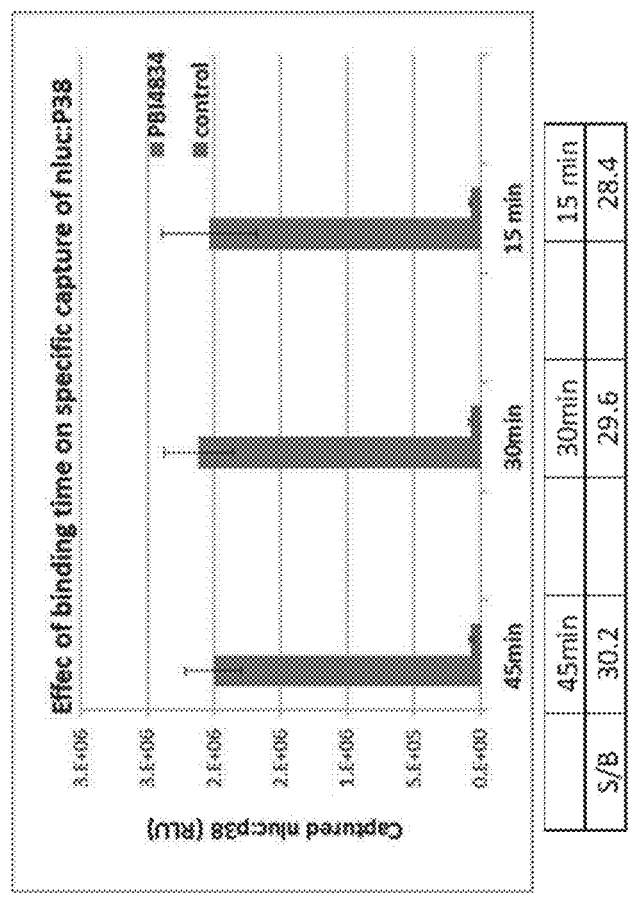
PBI-4834 (BIRB Carbamate Chloroalkane)

Figure 6
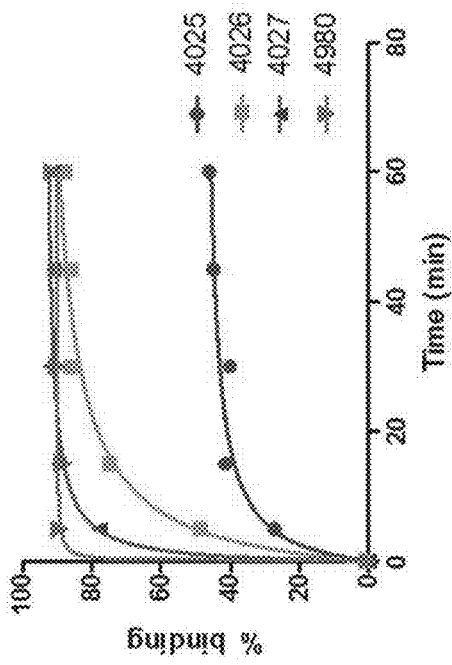
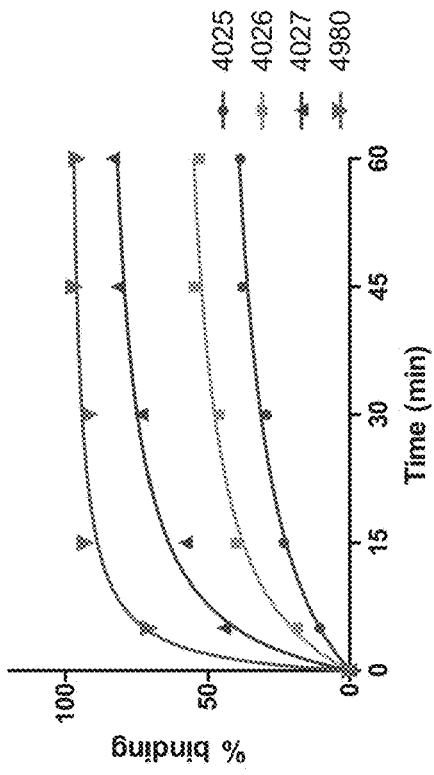

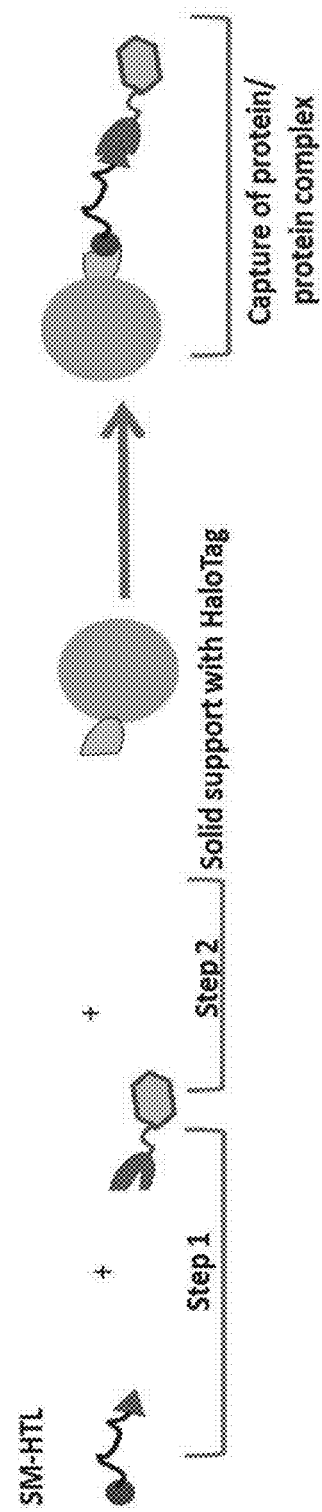

SUBSTRATES FOR COVALENT TETHERING OF PROTEINS TO FUNCTIONAL GROUPS OR SOLID SURFACES

CROSS-REFERENCE TO RELATED APPLICATION

The present application claims priority to U.S. Provisional Patent Application Ser. No. 61/788,257 filed Mar. 15, 2013, which is hereby incorporated by reference in its entirety.

FIELD

The present invention provides haloalkane substrates and linkers for connecting such substrates to functional elements (e.g., tags, labels, surfaces, etc.). Substrates and linkers described herein find use, for example, in labeling, detection and immobilization of proteins, cells and molecules. In particular, the linkers provided herein find use within substrates for dehalogenase variants that form covalent bonds with their haloalkane substrates.

BACKGROUND

Detection, isolation and immobilization of cells, proteins and molecules of interest are essential techniques for a variety of modern biological applications (e.g., basic molecular biology research, drug discovery, clinical diagnosis, etc.). Compositions and methods that provide advantages over existing techniques are in need.

SUMMARY

The present invention provides haloalkane substrates and linkers for connecting such substrates to functional elements (e.g., tags, labels, surfaces, etc.). Substrates and linkers described herein find use, for example, in labeling, detection and immobilization of proteins, cells and molecules. In particular, the linkers provided herein find use within substrates for dehalogenase variants that form covalent bonds with their haloalkane substrates.

In some embodiments, the present invention provides compounds of formula R-$L^1$-M-$L^2$-A-X; wherein R is a functional group, $L^1$ is a first linker portion, M is a carbamate group, $L^2$ is a second linker portion, A is an alkyl group, and X is a halogen; wherein $L^2$-A separates M and X by 6-18 linearly connected atoms; and wherein $L^1$ separates R and M by 2 or more linearly connected atoms. In some embodiments, A is $(CH_2)_6$. In some embodiments, $L^2$-A separates M and X by 12 linearly connected atoms. In some embodiments, the functional group comprises an affinity tag, fluorophore or solid surface. In some embodiments, $L^2$ does not comprise a carbamate group. In some embodiments, $L^2$ comprises linearly connected $CH_2$ and O groups. In some embodiments, $L^2$ consists of linearly connected $CH_2$ and O groups. In some embodiments, $L^2$ comprises $((CH_2)_2O)_x$, wherein x=0-5. In some embodiments, $L^2$ comprises $((CH_2)_2 O)_2$. In some embodiments, $L^1$ comprises linearly connected $CH_2$ and O groups. In some embodiments, $L^1$ comprises a carbamate. In some embodiments, $L^1$ comprises NHCOO—$((CH_2)_2O)_x$, wherein x=1-8. In some embodiments, $L^1$ comprises NHCOO—$((CH_2)_2O)_3$. In some embodiments, $L^1$ comprises NHCOO—$((CH_2)_2O)_3$, wherein $L^2$ comprises $((CH_2)_2O)_2$, and wherein A is $(CH_2)_6$.

PBI-4980 is an exemplary substrate of the formula R-$L^1$-M-$L^2$-A-X:

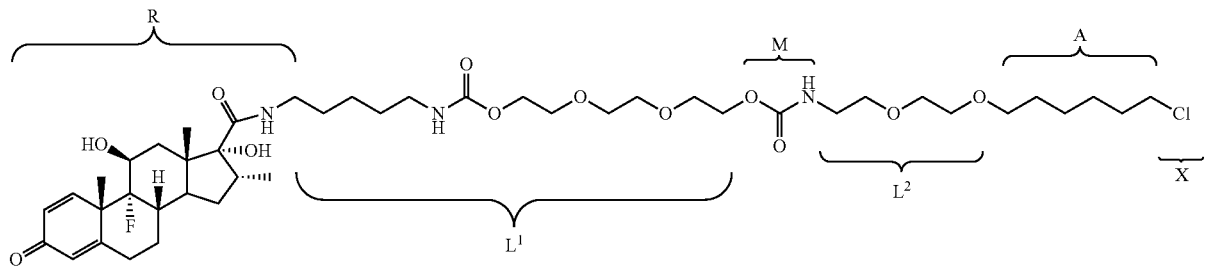

In some embodiments, the present invention provides compositions comprising a protein linked to a functional group by a linker comprising $L^1$-M-$L^2$-A; wherein $L^1$ is a first linker portion, M is a carbamate group, $L^2$ is a second linker portion, and A is an alkyl group; wherein $L^2$-A separates M from the protein by 8-16 (e.g., 10-14, 12) linearly connected atoms; and wherein $L^1$ separates the functional group and M by 2 or more linearly connected atoms. In some embodiments, the protein comprises a mutant dehalogenase. In some embodiments, the protein is part of a fusion protein. In some embodiments, A is $(CH_2)_6$. In some embodiments, $L^2$-A separates M and X by 12 linearly connected atoms. In some embodiments, the functional group comprises an affinity tag, fluorophore, or solid surface. In some embodiments, $L^2$ does not comprise a carbamate group. In some embodiments, $L^2$ comprises linearly connected $CH_2$ and O groups. In some embodiments, $L^2$ consists of linearly connected $CH_2$ and O groups. In some embodiments, $L^2$ comprises $((CH_2)_2O)_x$, wherein x=0-5. In some embodiments, $L^2$ comprises $((CH_2)_2O)_2$. In some embodiments, $L_1$ comprises linearly connected $CH_2$ and O groups. In some embodiments, $L_1$ comprises a carbamate. In some embodiments, $L^1$ comprises NHCOO—$((CH_2)_2O)_x$, wherein x=1-8. In some embodiments, $L^1$ comprises NHCOO—$((CH_2)_2O)_3$. In some embodiments, $L^1$ comprises NHCOO—$((CH_2)_2O)_3$, wherein $L^2$ comprises $((CH_2)_2 O)_2$, and wherein A is $(CH_2)_6$. In some embodiments, $L^1$ separates R and M by 1-15 linearly connected atoms (e.g., 1-12 atoms, 1-10 atoms, 2-10 atoms, 1-9 atoms, 2-9 atoms, 1-8 atoms, 2-8 atoms, 1-7 atoms, 1-6 atoms, 2-6 atoms, etc.).

In some embodiments, the present invention provides methods to detect or determine the presence or amount of a mutant dehalogenase, comprising: a) contacting a mutant dehalogenase with a dehalogenase substrate (e.g., R-$L^1$-M-$L^2$-A-X), wherein the mutant dehalogenase comprises at least one amino acid substitution relative to a corresponding wild-type dehalogenase, wherein the at least one amino acid substitution results in the mutant dehalogenase forming a bond with the substrate (e.g., $R-L^1-M-L^2-A-X$) which is more stable than the bond formed between the corresponding wild-type dehalogenase and the substrate, wherein the at least one amino acid substitution in the mutant dehalogenase is a substitution at an amino acid residue in the corresponding wild-type dehalogenase that is associated with activating a water molecule which cleaves the bond formed between the corresponding wild-type dehalogenase and the substrate or at an amino acid residue in the corresponding wild-type dehalogenase that forms an ester intermediate with the substrate; and b) detecting or determining the presence or amount of R, thereby detecting or determining the presence or amount of the mutant dehalogenase.

In some embodiments, the present invention provides methods to identify a target molecule for a compound of interest, comprising a) contacting a sample (e.g., cell or cell lysate) a with dehalogenase substrate (e.g., $R-L^1-M-L^2-A-X$), wherein the functional group is the compound of interest; b) contacting the sample and dehalogenase substrate mixture with a solid support comprising a mutant dehalogenase, wherein the mutant dehalogenase comprises at least one amino acid substitution relative to a corresponding wild-type dehalogenase, wherein the at least one amino acid substitution results in the mutant dehalogenase forming a bond with the substrate which is more stable than the bond formed between the corresponding wild-type dehalogenase and the substrate, wherein the at least one amino acid substitution in the mutant dehalogenase is a substitution at an amino acid residue in the corresponding wild-type dehalogenase that is associated with activating a water molecule which cleaves a bond formed between the corresponding wild-type dehalogenase and the substrate or at an amino acid residue in the corresponding wild-type dehalogenase that forms an ester intermediate with the substrate; and c) identifying the target molecule. In some embodiments, the compound of interest is a drug, drug compound, biomolecule or small molecule. In some embodiments, the target molecule is a protein. In some embodiments, the target molecule is a fusion protein. In some embodiments, the fusion protein is a fusion of the target molecule with a reporter protein, e.g., NanoLuc® luciferase.

In some embodiments, the present invention provides methods to label a cell, comprising: contacting a cell comprising a mutant dehalogenase with a dehalogenase substrate (e.g., $R-L^1-M-L^2-A-X$), wherein the mutant dehalogenase comprises at least one amino acid substitution relative to a corresponding wild-type dehalogenase, wherein the at least one amino acid substitution results in the mutant dehalogenase forming a bond with the substrate which is more stable than the bond formed between the corresponding wild-type dehalogenase and the substrate, wherein the at least one amino acid substitution in the mutant dehalogenase is a substitution at an amino acid residue in the corresponding wild-type dehalogenase that is associated with activating a water molecule which cleaves a bond formed between the corresponding wild-type dehalogenase and the substrate or at an amino acid residue in the corresponding wild-type dehalogenase that forms an ester intermediate with the substrate, thereby labeling the cell with the functional group, R.

In some embodiments, the present invention provides methods for detecting the presence or amount of a molecule in a cell, comprising: a) contacting a cell comprising a mutant dehalogenase with a dehalogenase substrate (e.g., $R-L^1-M-L^2-A-X$), wherein the mutant dehalogenase comprises at least one amino acid substitution relative to a corresponding wild-type dehalogenase, wherein the at least one amino acid substitution results in the mutant dehalogenase forming a bond with the substrate (e.g., $R-L^1-M-L^2-A-X$) which is more stable than the bond formed between the corresponding wild-type dehalogenase and the substrate; and b) detecting or determining the presence or amount of functional group, R, in the cell, thereby detecting the presence or amount of a molecule in a cell. In some embodiments, methods of detecting a molecule with a cell that interacts with a protein of interest are provided. In such embodiments, a fusion of a mutant dehalogenase and a protein of interest is used, along with the substrate, to capture molecular interactors (e.g., protein, small molecule, nucleic acid, etc.). The use of such reagents permits the capture of a molecule which interacts in the cell with the protein fused to the mutant dehalogenase, thereby identifying and/or capturing (isolating) the interacting molecule(s).

In some embodiments, the present invention provides methods to isolate a molecule of interest, comprising contacting (a) a solid support displaying a dehalogenase substrate (e.g., $R-L^1-M-L^2-A-X$) with (b) a fusion protein which comprises (i) a mutant dehalogenase that forms a covalent bond with the substrate (e.g., $R-L^1-M-L^2-A-X$) upon interaction with the substrate and (ii) a protein which is bound to the molecule of interest.

In some embodiments, the present invention provides methods to immobilize a protein of interest, comprising: contacting (a) a solid support comprising a substrate (e.g., $R-L^1-M-L^2-A-X$) with (b) a fusion of (i) a mutant dehalogenase that forms a covalent bond with the substrate (e.g., $R-L^1-M-L^2-A-X$) upon interaction with the substrate and (ii) a protein of interest.

In some embodiments, the present invention provides methods for preparing a compound of formula $R-L^1-M-L^2-A-X$ comprising coupling a compound of formula R—Y with a compound of formula $Z-L^1-M-L^2-A-X$, wherein Y and Z are groups that can react to link R- to $-Linker-L^1-M-L^2-A-X$. In some embodiments, R—Y is an activated ester of a compound of formula R and wherein Z is an amine suitable to react with the activated ester to form an amide bond.

In some embodiments, the present invention provides kits comprising a substrate ($R-L^1-M-L^2-A-X$) or substrate precursor (e.g., $Z-L^1-M-L^2-A-X$, R—Y, etc.) in combination (e.g., in same solution, separate containers but packaged together, etc.) with a mutant dehalogenase, reagents for carrying out assays, reagents for attaching functional groups to substrate precursor, positive/negative controls, instructions, cells (e.g., expressing a mutant dehalogenase or fusion thereof), etc. In some embodiments, the substrate or substrate precursor comprises a functional group that is a drug, drug compound, biomolecule or small molecule. In some embodiments, the present invention provides reaction mixtures comprising a substrate ($R-L^1-M-L^2-A-X$) or substrate precursor (e.g., $Z-L^1-M-L^2-A-X$, R—Y, etc.). In some embodiments, the present invention provides cells comprising a substrate ($R-L^1-M-L^2-A-X$) or substrate precursor (e.g., $Z-L^1-M-L^2-A-X$, R—Y, etc.) and/or a mutant dehalogenase or a fusion comprising a mutant dehalogenase. In some embodiments, the present invention provides solid surface displaying comprising a substrate ($R-L^1-M-L^2-A-X$) of the present invention.

BRIEF DESCRIPTION OF THE DRAWINGS

FIG. 1 shows the effect of binding time on the capture of a NanoLuc-p38 fusion protein in cells.

FIG. 6 shows the effect of linkers on the binding efficiency to a HaloTag® target protein from cell lysates (A) or cells (B) using chloroalkane-modified dexamethasone substrates.

FIG. 9 shows a schematic the pull-down method using HaloTag® protein beads.

DEFINITIONS

Figure 2:
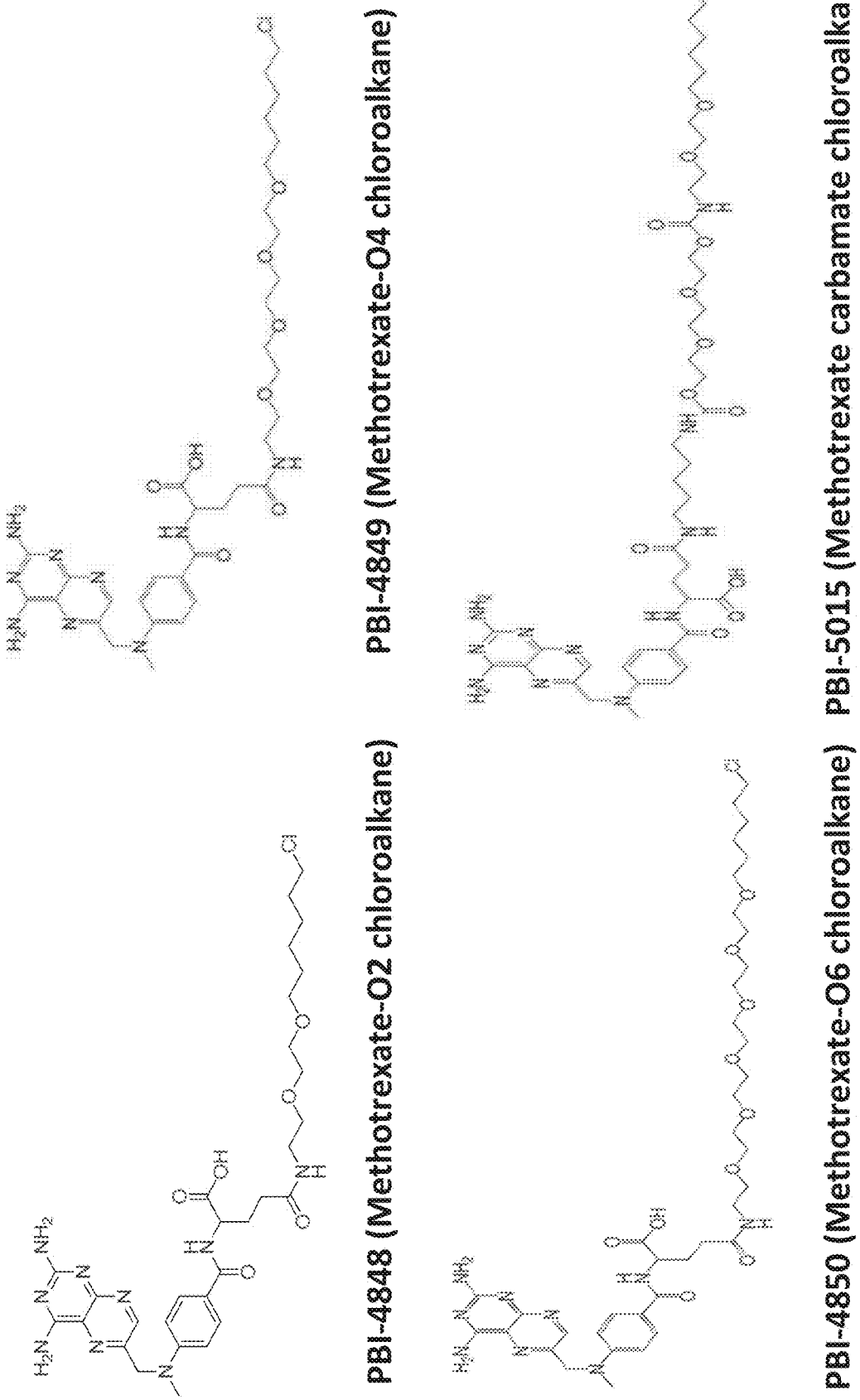
FIG. 2 provides structures of the substrates used in Example 3.

As used herein, the term "linearly connected atoms" refers to the backbone atoms of a chain or polymer, excluding pendant, side chain, or H atoms that do not form the main chain or backbone.

As used herein, the terms "fusion polypeptide" or "fusion protein" refer to a chimera of a polypeptide or protein of interest (e.g., luciferase, an affinity tag, targeting sequence, cellular target, protein to be analyzed) fused to a second polypeptide or protein (e.g., a mutant dehalogenase).

As used herein, the term "wild-type", refers to a gene or gene product that has the characteristics of that gene or gene product isolated from a naturally occurring source. A wild-type gene is that which is most frequently observed in a population and is thus arbitrarily designated the "wild-type" form of the gene. In contrast, the term "mutant" refers to a gene or gene product that displays modifications in sequence and/or functional properties (e.g., altered characteristics) when compared to the wild-type gene or gene product. It is noted that naturally-occurring mutants can be isolated; these are identified by the fact that they have altered characteristics when compared to the wild-type gene or gene product.

As used herein, the term "solid support" is used in reference to any solid or stationary material to which reagents such as substrates, mutant proteins, drug-like molecules, and other test components are attached. Examples of solid supports include microscope slides, wells of microtiter plates, coverslips, beads, particles, resin, cell culture flasks, as well as many other suitable items. The beads, particles or resin can be magnetic or paramagnetic.

As used herein, the term "compound of interest" is used to reference a drug, drug compound, biomolecule, small molecule, etc. that may bind to a target molecule, e.g., protein, nucleic acid, etc.

DETAILED DESCRIPTION

The present invention provides haloalkane substrates and linkers for connecting such substrates to functional elements (e.g., tags, labels, surfaces, etc.). Substrates and linkers described herein find use, for example, in labeling, detection and immobilization of proteins, cells and molecules. In particular, the linkers provided herein find use within substrates for dehalogenase variants that form covalent bonds with their haloalkane substrates.

The invention provides methods, compositions and kits for linking (e.g., via a covalent or otherwise stable bond) a protein (e.g., dehalogenase) or a fusion protein (e.g., dehalogenase fused to a protein of interest) to a functional group (e.g., tag, label, etc.) or solid surface (e.g., bead, array, slide, chip, tube, etc.). A protein is structurally related to a wild-type (native) protein (e.g., dehalogenase), but comprises at least one amino acid substitution relative to the corresponding wild-type protein (e.g., dehalogenase) that results in the protein forming stable (e.g., covalent) bond with the protein substrate (e.g., haloalkane substrate). The formation of the bond (e.g., covalent bond) between protein (e.g., dehalogenase) and substrate results in linking of the protein, and anything fused thereto, to the substrate and anything linked thereto. The aforementioned linking occurs, for instance, in solution or suspension, in a cell, on a solid support or at solution/surface interfaces.

A substrate typically includes a portion that is a reactive group linked, by a linker group, to one or more functional groups. As used herein, a "functional group" is a molecule which is detectable or is capable of detection (e.g., a chromophore, fluorophore or luminophore) or can be bound or attached to a second molecule (e.g., biotin, hapten, or a cross-linking group) or includes one or more amino acids, e.g., a peptide or polypeptide including an antibody or receptor, one or more nucleotides, lipids including lipid bilayers, a solid support, e.g., a sedimental particle, and the like. A functional group may have more than one property such as being capable of detection and being bound to another molecule. As used herein a "reactive group" is the portion of a substrate that is specifically recognized by a particular wild-type or mutant dehalogenase of the invention. The interaction of a reactive group in a substrate and a wild-type dehalogenase results in a product and the regeneration of the wild-type protein. However, interaction of the reactive group (e.g., haloalkane) with the mutant (e.g., dehalogenase) results in stable bond formation (e.g., covalent bond formation) between the protein and reactive group.

Systems comprising mutant proteins (e.g., mutant hydrolases (e.g., mutant dehalogenases) that covalently bind their substrates (e.g., haloalkane substrates) are described, for example, in U.S. Pat. Nos. 7,238,842; 7,425,436; 7,429,472; 7,867,726; each of which is herein incorporated by reference in their entireties.

In certain embodiments, the substrate is a substrate for a dehalogenase, e.g., a haloalkane dehalogenase, or a dehalogenase that cleaves carbon-halogen bonds in an aliphatic or aromatic halogenated substrate, such as a substrate for *Rhodococcus, Staphylococcus, Pseudomonas, Burkholderia, Agrobacterium* or *Xanthobacter* dehalogenase, or a substrate for a serine beta-lactamase. In some embodiments, a substrate optionally includes a linker which physically separates one or more functional groups from the reactive group in the substrate. For example, a substrate may include a linker of sufficient length, structure, charge, and hydrophobicity so that the one or more functional groups of the substrate do not disturb the interaction of the protein (e.g., dehalogease) and reactive group (e.g., haloalkane) of the substrate.

In some embodiments, a substrate comprises a compound of formula (I): R-$L^1$-M-$L^2$-A-X, wherein R is one or more functional groups; wherein the $L^1$ is a multiatom straight or branched chain including C, N, S, or O; M is a carbamate group; wherein the $L^2$ is a multiatom straight or branched chain including C, N, S, or O; wherein A is an alkane of at least 2 carbons (e.g., 2, 3, 4, 5, 6, 7, 8, 9, 10, 11, 12, etc.), wherein X is a halogen (e.g., Cl, F, Br, I, etc.), and wherein A-X is a substrate for a dehalogenase.

A. Reactive Groups

The reactive group of the substrate is the portion that is recognized by the mutant protein (e.g., mutant dehalogenase) and forms a covalent bond thereto. The reactive group may be any suitable substrate for any mutant protein that has been altered to form an ultra-stable or covalent bond with its substrate that would ordinarily only transiently bound by the protein. In particular embodiments, the protein is a mutant dehalogenase, and the reactive group of the substrate is a haloalkane. The haloalkane portion of the substrate comprises an alkane (e.g., $C_2$-$C_{20}$) capped by a terminal halogen (e.g., Cl, Br, F, I, etc.). In some embodiments, the haloalkane is of the formula A-X, wherein X is a halogen (e.g., Cl, Br, F, I, etc.), and wherein A is an alkane comprising 2-20 carbons. In certain embodiments, A comprises a straight-chain segment of 2-12 carbons. In certain embodiments, A is a straight-chain segment of 2-12 carbons.

B. Functional Groups

Functional groups (R) useful in the substrates and methods are molecules that are useful in the isolation, purification, detection, localization, immobilization, etc. of a substrate or a protein or fusion bound thereto. A functional group is capable of being covalently linked to one reactive substituent of a bifunctional linker or a substrate for a protein (e.g., dehalogenase), and, as part of a substrate, retains the desired property (e.g. activity, binding, etc.) as a functional group which is not linked to a substrate found in nature and is capable of forming a stable complex with a mutant protein (e.g., dehalogenase). Functional groups thus have one or more properties that facilitate detection, isolation, immobilization, etc. of stable complexes between a substrate having the functional group and a mutant protein (e.g., dehalogenase). A functional group may have more than one functional property, such as being capable of detection and of being bound to another molecule.

Functional groups include, but are not limited to, one or more small molecules (e.g., drugs, drug-like molecules), biomolecules, amino acids (e.g., a naturally occurring amino acid or a non-natural amino acid), a peptide or polypeptide (protein) including an antibody or a fragment thereof, a His-tag, a FLAG tag, a Strep-tag, an enzyme, a cofactor, a coenzyme, a peptide or protein substrate for an enzyme, for instance, a branched peptide substrate (e.g., Z-aminobenzoyl (Abz)-Gly-Pro-Ala-Leu-Ala-4-nitrobenzyl amide (NBA), a suicide substrate, or a receptor, one or more nucleotides (e.g., ATP, ADP, AMP, GTP or GDP) including analogs thereof, e.g., an oligonucleotide, double stranded or single stranded DNA corresponding to a gene or a portion thereof, e.g., DNA capable of binding a protein such as a transcription factor, RNA corresponding to a gene, for instance, mRNA which lacks a stop codon, or a portion thereof, double stranded RNA for RNAi or vectors therefor, a glycoprotein, a polysaccharide, a peptide-nucleic acid (PNA), lipids including lipid bilayers; or is a solid support, e.g., a sedimental particle such as a magnetic particle, a sepharose or cellulose bead, a membrane, glass, e.g., glass slides, cellulose, alginate, plastic or other synthetically prepared polymer (e.g., an eppendorf tube or a well of a multi-well plate, self-assembled monolayers, a surface plasmon resonance chip, or a solid support with an electron conducting surface, a drug (e.g., a chemotherapeutic such as doxorubicin, 5-fluorouracil, or camptosar (CPT-11; Irinotecan)), an aminoacylated tRNA such as an aminoacylated initiator tRNA or an aminoacylated amber suppressor tRNA, a molecule which binds $Ca^{2+}$, a molecule which binds $K^+$, a molecule which binds $Na^+$, a molecule which is pH sensitive, a radionuclide, a molecule which is electron opaque, a contrast agent, e.g., barium, iodine or other MRI or X-ray contrast agent, a molecule which fluoresces in the presence of NO or is sensitive to a reactive oxygen, a nanoparticle, e.g., an immunogold particle, paramagnetic nanoparticle, upconverting nanoparticle, or a quantum dot, a nonprotein substrate for an enzyme, an inhibitor of an enzyme, either a reversible or irreversible inhibitor, a chelating agent, a cross-linking group, for example, a succinimidyl ester or aldehyde, glutathione, biotin or other avidin binding molecule, avidin, streptavidin, cAMP, phosphatidylinositol, heme, a ligand for cAMP, a metal, NTA, and, in one embodiment, includes one or more dyes, e.g., a xanthene dye, a calcium sensitive dye, e.g., 1-[2-amino-5-(2,7-dichloro-6-hydroxy-3-oxy-9-xanthenyl)-phenoxy]-2-(2'-amino-5'-methylphenoxy)ethane-N,N,N',N'-tetraacetic acid (Fluo-3), a sodium sensitive dye, e.g., 1,3-benzenedicarboxylic acid, 4,4'-[1,4,10,13-tetraoxa-7,16-diazacyclooctadecane-7,16-diylbis(5-methoxy-6,2-benzofurandiyl)]bis (PBFI), a NO sensitive dye, e.g., 4-amino-5-methylamino-2',7'-difluorescein, or other fluorophore (e.g., carboxy rhodamine analog, see e.g., U.S. Ser. No. 13/682,589. In some embodiments, the functional group is a hapten or an immunogenic molecule, e.g., one which is bound by antibodies specific for that molecule. In some embodiments, the functional group is not a radionuclide. In other embodiments, the functional group is a radionuclide, e.g., $^3H$, $^{14}C$, $^{35}S$, 125I, $^{131}I$, including a molecule useful in diagnostic methods.

In certain embodiments, functional groups have a detectable property that allows for detection of a substrate and/or a protein or fusion bound thereto. Detectable functional groups include those with a characteristic electromagnetic spectral property such as emission or absorbance, magnetism, electron spin resonance, electrical capacitance, dielectric constant or electrical conductivity as well as functional groups which are ferromagnetic, paramagnetic, diamagnetic, luminescent, electrochemiluminescent, fluorescent, phosphorescent, chromatic, antigenic, or have a distinctive mass. A functional group includes, but is not limited to, a nucleic acid molecule (e.g., DNA or RNA (e.g., an oligonucleotide or nucleotide), a protein (e.g., a luminescent protein, a peptide, a contrast agent (e.g., MRI contract agent), a radionuclide an affinity tag (e.g., biotin or streptavidin), a hapten, an amino acid, a lipid, a lipid bilayer, a solid support, a fluorophore, a chromophore, a reporter molecule, a radionuclide, an electron opaque molecule, a MRI contrast agent (e.g., manganese, gadolinium(III) or iron-oxide particles), and the like. Methods to detect a particular functional group, or isolate a substrate and anything bound thereto, are known to the art.

Exemplary functional groups include haptens (e.g., molecules useful to enhance immunogenicity such as keyhole limpet hemacyanin), cleavable labels (e.g., photocleavable biotin) and fluorescent labels (e.g., N-hydroxysuccinimide (NHS) modified coumarin and succinimide or sulfonosuccinimide modified BODIPY (which can be detected by UV and/or visible excited fluorescence detection), rhodamine (R110, rhodols, CRG6, Texas Methyl Red (TAMRA), Rox5, FAM, or fluoroscein), coumarin derivatives (e.g., 7 aminocoumarin, and 7-hydroxycoumarin, 2-amino-4-methoxynapthalene, 1-hydroxypyrene, resorufin, phenalenones or benzphenalenones (U.S. Pat. No. 4,812,409)), acridinones (U.S. Pat. No. 4,810,636), anthracenes, and derivatives of alpha and beta-napthol, fluorinated xanthene derivatives including fluorinated fluoresceins and rhodols (e.g., U.S. Pat. No. 6,162,931), and bioluminescent molecules (e.g., luciferase (e.g., Oplophorus-derive luciferase (See e.g., U.S. application Ser. No. 12/773,002; U.S. application Ser. No. 13/287,986; herein incorporated by reference in their entireties) or GFP or GFP derivatives). A fluorescent (or bioluminescent) functional group linked to a mutant protein (e.g., dehalogenase) by virtue of being linked to a substrate for a corresponding wild-type protein (e.g., dehalogenase), may be used to sense changes in a system, like phosphorylation, in real-time. Moreover, a fluorescent molecule, such as a chemosensor of metal ions in a substrate may be employed to label proteins which bind the substrate. A bioluminescent or fluorescent functional group such as BODIPY, rhodamine green, GFP, or infrared dyes, also finds use as a functional group and may, for instance, be employed in interaction studies (e.g., using BRET, FRET, LRET or electrophoresis).

Another class of functional group is a molecule that selectively interacts with molecules containing acceptor groups (an "affinity" molecule). Thus, a substrate for a protein (e.g., dehalogenase) which includes an affinity molecule can facilitate the separation of complexes having such a substrate and a mutant protein because of the selective interaction of the affinity molecule with another molecule (e.g., an acceptor molecule that may be biological or non-biological in origin). For example, the specific molecule with which the affinity molecule interacts (referred to as the acceptor molecule) could be a small organic molecule, a chemical group such as a sulfhydryl group (—SH) or a large biomolecule such as an antibody or other naturally occurring ligand for the affinity molecule. The binding is normally chemical in nature and may involve the formation of covalent or non-covalent bonds or interactions such as ionic or hydrogen bonding. The acceptor molecule might be free in solution or bound to a solid or semi-solid surface, a polymer matrix or reside on the surface of a solid or semi-solid substrate. The interaction may also be triggered by an external agent such as light, temperature, pressure or the addition of a chemical or biological molecule that acts as a catalyst. The detection and/or separation of the complex from the reaction mixture occurs because of the interaction, normally a type of binding, between the affinity molecule and the acceptor molecule.

Examples of affinity molecules include molecules such as immunogenic molecules (e.g., epitopes of proteins, peptides, carbohydrates or lipids (e.g., any molecule which is useful to prepare antibodies specific for that molecule)); biotin, avidin, streptavidin, and derivatives thereof; metal binding molecules; and fragments and combinations of these molecules. Exemplary affinity molecules include H is S(HHHHH), His×6 (HHHHHH), C-myc (EQKLISEEDL), Flag (DYKDDDDK), SteptTag (WSHPQFEK), HA Tag (YPYDVPDYA), thioredoxin, cellulose binding domain, chitin binding domain, S-peptide, T7 peptide, calmodulin binding peptide, C-end RNA tag, metal binding domains, metal binding reactive groups, amino acid reactive groups, inteins, biotin, streptavidin, and maltose binding protein. For example, a substrate for a protein (e.g., dehalogenase) which includes biotin is contacted with a mutant protein (e.g., dehalogenase). A covalent bond is formed between the protein (e.g., dehalogenase) and the reactive group of the substrate. The presence of the biotin in a complex between the mutant protein and the substrate permits selective binding of the complex to avidin molecules (e.g., streptavidin molecules coated onto a surface (e.g., beads, microwells, nitrocellulose and the like)). Suitable surfaces include resins for chromatographic separation, plastics such as tissue culture surfaces or binding plates, microtiter dishes and beads, ceramics and glasses, particles including magnetic particles, polymers and other matrices. In some case, these materials may be part of biomolecular sensing devices such as optical fibers, chemfets, and plasmon detectors.

Another example of an affinity molecule is dansyllysine. Antibodies which interact with the dansyl ring are commercially available (Sigma Chemical; St. Louis, Mo.) or can be prepared using known protocols such as described in Antibodies: A Laboratory Manual (Harlow and Lane, 1988). For example, the anti-dansyl antibody is immobilized onto the packing material of a chromatographic column. This method, affinity column chromatography, accomplishes separation by causing the complex between a mutant hydrolase and a substrate to be retained on the column due to its interaction with the immobilized antibody, while other molecules pass through the column. The complex may then be released by disrupting the antibody-antigen interaction. Specific chromatographic column materials such as ion-exchange or affinity Sepharose, Sephacryl, Sephadex and other chromatography resins are commercially available (Sigma Chemical; St. Louis, Mo.; Pharmacia Biotech; Piscataway, N.J.). Dansyllysine may conveniently be detected because of its fluorescent properties.

When employing an antibody as an acceptor molecule, separation can also be performed through other biochemical separation methods such as immunoprecipitation and immobilization of antibodies on filters or other surfaces such as beads, plates or resins. For example, complexes of a mutant hydrolase and a substrate may be isolated by coating magnetic beads with an affinity molecule-specific or a hydrolase-specific antibody. Beads are oftentimes separated from the mixture using magnetic fields.

Another class of functional molecules includes molecules detectable using electromagnetic radiation and includes, but is not limited to, xanthene fluorophores, dansyl fluorophores, coumarins and coumarin derivatives, fluorescent acridinium moieties, benzopyrene based fluorophores, as well as 7-nitrobenz-2-oxa-1,3-diazole, and 3-N-(7-nitrobenz-2-oxa-1,3-diazol-4-yl)-2,3-diamino-propionic acid. Preferably, the fluorescent molecule has a high quantum yield of fluorescence at a wavelength different from native amino acids and more preferably has high quantum yield of fluorescence that can be excited in the visible, or in both the UV and visible, portion of the spectrum. Upon excitation at a preselected wavelength, the molecule is detectable at low concentrations either visually or using conventional fluorescence detection methods. Electrochemiluminescent molecules such as ruthenium chelates and its derivatives or nitroxide amino acids and their derivatives are detectable at femtomolar ranges and below.

In addition to fluorescent molecules, a variety of molecules with physical properties based on the interaction and response of the molecule to electromagnetic fields and radiation can be used to detect complexes between a mutant hydrolase and a substrate. These properties include absorption in the UV, visible and infrared regions of the electromagnetic spectrum, presence of chromophores which are Raman active, and can be further enhanced by resonance Raman spectroscopy, electron spin resonance activity and nuclear magnetic resonances and molecular mass, e.g., via a mass spectrometer.

Methods to detect and/or isolate complexes having affinity molecules include chromatographic techniques including gel filtration, fast-pressure or high-pressure liquid chromatography, reverse-phase chromatography, affinity chromatography and ion exchange chromatography. Other methods of protein separation are also useful for detection and subsequent isolation of complexes between a mutant hydrolase and a substrate, for example, electrophoresis, isoelectric focusing and mass spectrometry.

In certain embodiments, a functional group is cell permeable (e.g., in the context of the substrate, alone). In some embodiments, a functional group added extracellularly is capable of crossing the cell membrane to enter a cell (e.g., via diffusion, endocytosis, active transport, passive transport, etc.).

C. Linkers

In some embodiments, substrates of the present invention comprise a linker or linkers between the functional and reactive groups (e.g., $L^1$-M-$L^2$). In some embodiments, the linker provides sufficient distance to allow the protein (e.g., dehalogenase) to interact with (e.g., covalently bind) the reactive portion of the substrate. A linker, as used herein, is not a single covalent bond. The linker provides a substrate that can be bound by its target protein (e.g., dehalogenase). In some embodiments, the linker separates a functional group (R) and the reactive group (A-X) by about 5 angstroms to about 1000 angstroms, inclusive, in length. Other suitable linkers include linkers that separate R and the reactive group by about 5 angstroms to about 100 angstroms, as well as linkers that separate R and the substrate by about 5 angstroms to about 50 angstroms, by about 5 angstroms to about 25 angstroms, by about 5 angstroms to about 500 angstroms, or by about 30 angstroms to about 100 angstroms.

In particular embodiments, a linker comprises a carbamate group. For example, a substrate may comprise R-$L^1$-M-$L^2$-A-X, wherein R is a functional group, $L^1$ is a first linker portion, M is a carbamate group (e.g., OCONH, NHCOO, etc.), $L^2$ is a second linker portion, A is an alkyl group, and X is a halogen. In some embodiments, the carbamate is oriented such the nitrogen end is oriented toward the reactive group. In some embodiments, the carbamate is oriented such that the oxygen end is oriented toward the reactive group. In some embodiments, a linker comprises a single carbamate group. In some embodiments, a linker comprises two or more carbamate groups (e.g., 2, 3, 4, 5, 6, 7, 8, etc.). In some embodiments, in which there are multiple carbamates, M is the carbamate closest to the reactive group (e.g., A-X) and other carbamate groups are part of $L^1$. In some embodiments, one or both of $L^1$ and/or $L^2$ independently comprise alkyl groups (e.g., methyl, ethyl, propyl, butyl, pentyl, hexyl, etc.). In other embodiments, one or both of $L^1$ and/or $L^2$ independently comprise —(($CH_2$)$_2$O)$_p$— or —(O($CH_2$)$_2$)$_p$— groups, wherein p=1-10. In some embodiments, one or both of $L^1$ and/or $L^2$ are absent from a substrate (e.g., R-$L^1$-M-A-X or R-M-$L^2$-A-X).

In certain embodiments, $L_1$ is a cleavable linker portion. In some embodiments, $L_1$ is enzyme cleavable, chemically cleavable, photocleavable, etc. In some embodiments, cleavage of $L_1$, results in release of the mutant protein (e.g., mutant dehalogenase) from the functional group (e.g., fluorophore, solid surface, etc.).

In some embodiments, a linker is configured to separate X (halogen) and M (carbamate) by a distance that optimizes the interaction between the substrate and protein (e.g., dehalogenase). In certain embodiments, X and M are separated by 6-18 linearly connected atoms (e.g., ($CH_2$)$_6$O ($CH_2$)$_2$ O($CH_2$)$_2$, ($CH_2$)$_{6-18}$, etc.). In some embodiments, A and $L_2$ comprise 6-18 linearly connected atoms (e.g., 6, 7, 8, 9, 10, 11, 12, 13, 14, 15, 16, 17, 18). In some embodiments, A and $L^2$ comprises 9-15 linearly connected atoms (e.g., 9, 10, 11, 12, 13, 14, 15). In some embodiments, A and $L^2$ comprises 12 linearly connected C, N, and/or O atoms (e.g., ($CH_2$)$_6$O($CH_2$)$_2$O($CH_2$)$_2$, ($CH_2$)$_6$($CH_2$)$_3$O($CH_2$)$_2$, ($CH_2$)$_6$O ($CH_2$)$_2$($CH_2$)$_3$, etc.).

In some embodiments, a linker is configured to separate R (functional group) and M (the linker carbamate closest to the X) by a distance that decreases the interaction between the functional group and protein (e.g., dehalogenase). In some embodiments, $L^1$ comprises more than 1 linearly connected C, S, N, and/or O atoms. In some embodiments, $L^1$ comprises one or more carbamate groups. In some embodiments, $L^1$ comprises one or more alkyl groups (e.g., methyl, ethyl, propyl, butyl, pentyl, hexyl, etc.). In some embodiments, $L^1$ comprises one or more O($CH_2$)$_2$ or ($CH_2$)O groups. In some embodiments, $L^1$ comprises 1-10 linearly connected atoms (e.g., 1-9, 2-9, 1-8, 2-8, 1-7, 2-7, 1-6, 2-6, etc.). In some embodiments, $L^1$ is 1-10 linearly connected atoms (e.g., 1-9, 2-9, 1-8, 2-8, 1-7, 2-7, 1-6, 2-6, etc.) in length.

In certain embodiments, a linker is a carbamate-containing chain that separates the functional group from the reactive group. In some embodiments, the reactive-group proximate carbamate group is separated from the halogen (X) by 12 linearly connected atoms (e.g., C, N, O, S, etc.). In some embodiments, the reactive-group proximate carbamate group is separated from the halogen (X) by a combination of $CH_2$ and O groups totaling 10-14 linearly connected atoms (e.g., 12 atoms). In some embodiments, the reactive-group-proximate carbamate group is separated from the functional group (R) by 2-24 linearly connected atoms (e.g., C, N, O, S, etc.). In some embodiments, the reactive-group proximate carbamate group is separated from the functional group (R) by a combination of NH, NHCOO, CO, $CH_2$ and O groups totaling 2-24 linearly connected atoms (e.g., 12 atoms).

In some embodiments, a linker comprises a carbamate separated from the functional group by at least 2 linearly connected C, N, O, or S atom (e.g., 2-50 atoms, 2-40 atoms, 2-30 atoms, 2-20 atoms, 2-10 atoms, etc.) and separated from the halogen (X) by 8-16 linearly connected C, N, O, or S atoms (e.g., 10-14 atoms, 11-13 atoms, 12 atoms). In some embodiments, a linker meets the above criteria and comprises one or more backbone groups selected from of: —O—, —S—, —CH=CH—, =C=, a carbon-carbon triple bond, C=O, NH, SH, OH, CN, etc. In some embodiments, a linker comprises one or more substituents, pendants, side chains, etc. comprising any suitable organic functional groups.

D. Substrates

As described above, substrates comprise a functional group and reactive group connected by a linker (e.g., carbamate-containing linker). In some embodiments, a carbamate of the linker is separated from the functional group by two or more linearly connected atoms. In some embodiments, the carbamate of the linker that is located closest to the reactive group is separated from the reactive group by 8-16 linearly connected atoms (e.g., 10-14 atoms, 11-13 atoms, 12 atoms).

In some embodiments, substrates are permeable to plasma membranes of cells. In certain embodiments, the presence of a carbamate (M) between the linker portions ($L^1$ and $L^2$) provides an unexpected degree of cell permeability despite alterations to other portions of the substrate (e.g., lengthening of $L^1$, $L^2$, or substrate as a whole). In some embodiments, substrates comprising carbamate (e.g., at position M) maintain cell permeability at lengths in which substrates lacking a carbamate (e.g., amide linkers) are cell impermeable (See, e.g., Examples 3-4). In some embodiments, substrates efficiently enter cells when added to cell media or administered to the cells. In particular embodiments, substrates are rapidly and efficiently loaded into and washed out of cells in the absence of a mutant protein (e.g., dehalogenase). In the presence of a mutant protein (e.g., dehalogenase), at least a portion of the substrate is bound within the cell and prevented from being washed out. Thus, the bound portion of the substrate can serve as a marker or as a mechanism to capture the mutant protein (e.g., dehalogenase) or a fusion thereof. In other embodiments (e.g., when the functional group is a solid surface), substrates are not permeable to the plasma membranes of cells. In some embodiments, a substrate comprises a cell permeable functional group (e.g., not a solid surface).

In certain embodiments, substrates (e.g., comprising bulky functional groups (e.g., functional groups that cannot fit within the active site of the mutant protein (or a channel thereto)) must be of sufficient length to allow the reactive group access to the active site of a mutant protein (e.g., mutant dehalogenase) while allowing the functional group to remain on the exterior of the mutant protein. With many substrates, additional length (e.g., beyond an optimal point) results in reduction in binding affinity or cell permeability. In some embodiments, substrates comprising carbamate (e.g., at position M) maintain high binding affinity (e.g., for mutant protein (e.g., mutant dehalogenase)), binding kinetics, and/or cell permeability at lengths in which substrates lacking a carbamate (e.g., substrates comprising amide linkers) exhibit reduced performance (See, e.g., Examples 3-4).

In certain embodiments, substrates include two or more functional groups. In some embodiments, one of the functional groups is an enzyme. In other embodiments, one of the functional groups is a substrate for an enzyme. For example, one functional group may be luciferin and the other a protease recognition site (e.g., one which contains sequences sufficient for recognition by the protease including the site to be cleaved), one functional group may be an affinity tag (e.g., biotin) and the other a fluorophore, or one functional group may be a protease recognition site and the other a fluorophore. A substrate may comprise any combination of two or more of the functional groups described herein or understood in the art.

In some embodiments, the present invention provides compositions and methods for the synthesis and/or production of the substrates described herein. The invention further provides methods for preparing a substrate for a dehalogenase which is modified to include one or more functional groups.

E. Mutant Dehalogenase

A mutant protein, hydrolase and/or dehalogenase, as described in more detail in, for example, U.S. Pat. Nos. 7,238,842; 7,425,436; 7,429,472; 7,867,726; each of which is herein incorporated by reference in their entireties, comprises at least one amino acid substitution relative to a corresponding wild-type protein, hydrolase or dehalogenase. Mutant proteins (e.g., mutant dehalogenases) are not limited to those prepared via recombinant techniques (e.g., site-directed mutagenesis or recursive mutagenesis) and comprise one or more amino acid substitutions which render the mutant protein (e.g., mutant dehalogenase) capable of forming a stable (e.g., covalent) bond with a substrate, such as a substrate comprising one or more functional groups. In some embodiments, the mutant proteins are mutant hydrolases. In certain embodiments, the mutant proteins are mutant dehalogenases. The at least one amino acid substitution results in the mutant protein forming a bond with the substrate which is more stable than the bond formed between the corresponding wild-type protein and the substrate (e.g., a covalent bond). The at least one amino acid substitution in the mutant protein is a substitution at an amino acid residue in the corresponding wild-type protein that is associated with activating a water molecule which cleaves the bond formed between the corresponding wild-type protein and the substrate or at an amino acid residue in the corresponding wild-type protein that forms an ester intermediate with the substrate. In some embodiments, the mutant protein comprises at least two amino acid substitutions relative to a corresponding wild-type protein, wherein one substitution is in a residue which, in the wild-type protein, is associated with activating a water molecule or in a residue which, in the wild-type protein, forms an ester intermediate by nucleophilic attack of a substrate for the hydrolase, and another substitution in a residue which, in the wild-type protein, is at or near a binding site(s) for a hydrolase substrate, but is not in a residue that in the corresponding wild-type protein is associated with activating a water molecule or which forms ester intermediate with a substrate. In one embodiment, the second substitution is in a residue which, in the wild-type protein lines the site(s) for substrate entry into the catalytic pocket of the protein. The additional substitution(s) preferably increase the rate of stable covalent bond formation of those mutants binding to a substrate of a corresponding wild-type protein. Details of the sequences and mutations of proteins, hydrolases and dehalogenases are described, for example, in U.S. Pat. Nos. 7,238,842; 7,425,436; 7,429,472; 7,867,726; each of which is herein incorporated by reference in their entireties.

F. Fusions

In various embodiments, the present invention provides fusion proteins comprising a mutant protein (e.g., mutant dehalogenase) and amino acid sequences of a protein or peptide of interest (e.g., a drug target, a marker protein (e.g., a selectable marker protein, affinity tag (e.g., a polyhistidine sequence))), an enzyme of interest (e.g., luciferase, RNasin, RNase, and/or GFP), a nucleic acid binding protein, an extracellular matrix protein, a secreted protein, an antibody or a portion thereof such as Fc, a bioluminescence protein, a receptor ligand, a regulatory protein, a serum protein, an immunogenic protein, a fluorescent protein, a protein with reactive cysteines, a receptor protein (e.g., NMDA receptor, a channel protein (e.g., an ion channel protein such as a sodium-, potassium- or a calcium-sensitive channel protein including a HERG channel protein)), a membrane protein, a cytosolic protein, a nuclear protein, a structural protein, a phosphoprotein, a kinase, a signaling protein, a metabolic protein, a mitochondrial protein, a receptor associated protein, a fluorescent protein, an enzyme substrate (e.g., a protease substrate), a transcription factor, a protein destabilization sequence, or a transporter protein (e.g., EAAT1-4 glutamate transporter), as well as targeting signals (e.g., a plastid targeting signal, such as a mitochondrial localization sequence, a nuclear localization signal or a myristilation sequence, that directs the mutant hydrolase to a particular location).

In certain embodiments, a fusion protein is expressed from a recombinant DNA which encodes the mutant protein (e.g. mutant dehalogenase) and at least one protein of interest or formed by chemical synthesis. The protein of interest may be fused to the N-terminus or the C-terminus of the mutant hydrolase. In some embodiments, the fusion protein comprises a protein of interest at the N-terminus and another protein, e.g., a different protein, at the C-terminus, of the mutant protein (e.g., mutant dehalogenase). For example, the protein of interest may be a fluorescent protein or an antibody. Optionally, the proteins in the fusion are separated by a connector sequence (e.g., one having at least 2 amino acid residues, such as one having 13 to 17 amino acid residues). The presence of a connector sequence in a fusion protein does not substantially alter the function of either protein in the fusion relative to the function of each individual protein. Thus, for a fusion of a mutant dehalogenase and a luciferase (e.g., *Renilla* luciferase, Oplophorus-derive luciferase (See e.g., U.S. application Ser. No. 12/773, 002; U.S. application Ser. No. 13/287,986; herein incorporated by reference in their entireties)), the presence of a connector sequence does not substantially alter the stability of the bond formed between the mutant dehalogenase and a substrate therefor or the activity of the luciferase. For any particular combination of proteins in a fusion, a wide variety of connector sequences may be employed. In some embodiments, the connector sequence is a sequence recognized by an enzyme (e.g., a cleavable sequence (e.g., enzyme cleavable, chemically cleavable, photocleavable, etc.)).

G. Kits

The invention also provides compositions and kits comprising a substrate described herein (e.g., in combination with a mutant protein that forms a covalent bond with the substrate). In some embodiments, the kit includes a substrate described herein, wherein the functional group is a compound of interest (e.g., drug, drug compound, biomolecule or small molecule) and a solid support comprising a mutant dehalogenase. In some embodiments, a kit includes a solid support comprising a substrate of the invention, a solid support comprising a mutant protein or a fusion thereof, a kit comprising a substrate of the invention, or a kit comprising a vector encoding a dehalogenase or a fusion thereof. In some embodiments, kits further comprise: reagents for performing assays, reagents for adding functional groups onto linker/reactive groups, positive and/or negative controls, instructions, etc.

H. Applications

The substrates and mutant proteins (e.g., dehalogenases) are useful to isolate, detect, identify, image, display, or localize molecules of interest, label cells, including live cell imaging, or label proteins in vitro and/or in vivo. For instance, a substrate bound to a solid support (e.g., microsphere, membrane, polymeric plate, beads (e.g., glass, magnetic polymeric, etc.), glass slides, and the like), or a mutant protein (e.g., dehalaogenase) bound to a solid support may be used to generate protein arrays, cell arrays, vesicle/organelle arrays, gene arrays, and/or cell membrane arrays. Thus, in some embodiments, methods are provided to isolate or identify a molecule of interest. In some embodiments, the method includes contacting a sample (e.g., cell or cell lysate) with a substrate described herein, wherein the functional group is a compound of interest (e.g., drug, drug compound, biomolecule or small molecule) and a solid support comprising a mutant dehalogenase. The molecule of interest bound to the substrate can then be identified. In some embodiments, the method includes contacting a sample comprising one or more fusion proteins at least one of which comprises a mutant protein (e.g., dehalogenase) and a protein which is bound to the molecule of interest and a solid support comprising one or more substrates described herein. For instance, the method may be employed to isolate DNA bound to a protein fused to a mutant protein.

In some embodiments, methods are provided to detect or determine the presence or amount of a mutant protein (e.g., mutant dehalogenase) or a fusion thereof. The method includes contacting a mutant protein (e.g., mutant dehalogenase) with a substrate which comprises one or more functional groups. The mutant protein and substrate, upon interaction within a sample, cell, etc. form a covalent bond. Unbound substrate may be washed away. The presence or amount of the functional group is detected or determined, thereby detecting or determining the presence or amount of the mutant protein (e.g., mutant dehalogenase). In some embodiments, the mutant protein is in or on the surface of a cell. In other embodiments, the mutant protein is in a cell lysate.

Also provided are methods of using a mutant protein (e.g., mutant dehalogenase) and substrate to isolate a molecule or to detect or determine the presence or amount of, location (e.g., intracellular, subcellular or extracellular location), or movement of certain molecules in cells. In one embodiment, a method to isolate a molecule of interest in a sample is provided. The method includes contacting a sample with a fusion protein comprising a mutant protein (e.g., mutant dehalogenase) and a protein which binds a molecule of interest with a substrate for the mutant protein (e.g., mutant dehalogenase) which comprises one or more functional groups. In some embodiments, at least one functional group is a solid support or a molecule which binds to a solid support. In some embodiments, the sample contains intact cells, while in other embodiments the sample is a cell lysate or subcellular fraction. Then, the molecule of interest is isolated.

In some embodiments, the invention includes method to isolate a protein of interest. The method includes contacting a fusion protein comprising a mutant protein (e.g., mutant dehalogenase) and a protein of interest with a substrate which comprises at least one functional group. In some embodiments, at least one functional group is a solid support or a molecule which binds to a solid support. Then, the protein of interest is isolated.

In other embodiments, the invention includes a method to identify an agent that alters the interaction of a protein of interest with a molecule suspected of interacting with the protein of interest. The method includes contacting at least one agent with the molecule suspected of interacting with the protein of interest, a fusion protein comprising mutant protein (e.g., mutant dehalogenase) and the protein of interest, and a substrate which comprises one or more functional groups. In some embodiments, at least one functional group is a solid support or a molecule which binds to a solid support. Then, it is determined whether the agent alters the interaction between the protein of interest and the molecule suspected of interacting with the protein of interest.

Moreover, a substrate bound to a solid support or a mutant dehalogenase bound to a solid support may be used to generate protein arrays, cell arrays, vesicle/organelle arrays and cell membrane arrays.

In certain embodiments, methods to monitor the expression, location and/or movement (trafficking) of proteins in a cell as well as to monitor changes in microenvironments within a cell are provided.

To isolate, sort or purify cells, the mutant protein (e.g., mutant dehalogenase) may be expressed on the outside surface of cells (e.g., via a fusion with a plasma membrane protein). To isolate, purify or separate organelles, the mutant protein (e.g., mutant dehalogenase) is expressed on the cytosolic surface of the organelle of interest. In another embodiment, to create an optimal platform for growing different cells, the mutant protein (e.g., mutant dehalogenase) is fused with an extracellular matrix component or an outer membrane protein and tethered to a three-dimensional cell culture or a platform for tissue engineering. As an example, primary neurons or embryonic stem cells may be grown on the platform to form a feeder layer.

Other applications include detecting or labeling cells. Thus, the use of a mutant protein (e.g., mutant dehalogenase) and a corresponding substrate permits the detection of cells, for instance, to detect cell migration in vitro or in vivo after implantation or injection into animals (e.g., angiogenesis/chemotaxis assays, migration of implanted neurons, normal, malignant, or recombinantly-modified cells implanted/injected into animals, and the like), and live cell imaging followed by immunocytochemistry. In other embodiments, the invention provides a method to label newly synthesized proteins. For example, cells comprising a vector which expresses a mutant protein (e.g., mutant dehalogenase) or a fusion thereof, are contacted with a substrate which lacks a functional group. Cells are then contacted with an agent (e.g., an inducer of gene expression), and a substrate for the mutant protein (e.g. mutant dehalogenase) which contains one or more functional groups. The presence, amount or location of the mutant protein (e.g., mutant dehalogenase) or fusion thereof is then detected or determined. The presence, amount or location of the mutant protein (e.g., mutant dehalogenase) or fusion thereof is due to newly synthesized mutant hydrolase or a fusion thereof. Alternatively, cells comprising a vector which expresses a mutant protein (e.g., mutant dehalogenase) or a fusion 20080070299; 20080026407; 20070224620; 20070212762; 20060127988; 20050164321; 20050130205; and 20040146987; each of which is herein incorporated by reference in its entirety.

EXPERIMENTAL

Example 1

Dexamethasone Cadaverine Intermediate

To a solution of dexamethasone acid (10 mg, 26 umol, Toronto Research Chemicals) and (Benzotriazol-1-yloxy) tripyrrolidinophosphonium hexafluorophosphate (PyBOP, 15 mg, 29 umol) in 2 mL of DMF, N-Boc cadaverine (106 mg, 520 umol) was added. The reaction was stirred for 16 h then quenched by addition of 1 N HCl and the product was isolated by preparative HPLC eluting with 10→50% MeCN in aqueous 0.1% formic acid, which provided the desired dexamethasone N-Boc cadaverine adduct that was carried on directly.

Dexamethasone N-Boc-cadaverine adduct (24 mg, 38 umol) was treated with 4 M HCl in dioxane (0.5 mL) at RT. Upon completion of the reaction, it was then partitioned between $CH_2Cl_2$ and $NaHCO_3$ (0.05M aq). The layers were separated, and the organic layer dried and concentrated to give the desired dexamethasone cadaverine intermediate (12 mg) that was used without further purification.

PBI-4980: Dexamethasone Carbamate Chloroalkane

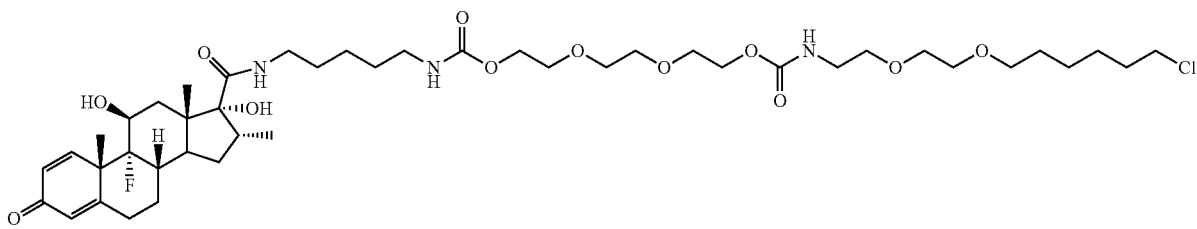

thereof, are contacted with a substrate for the protein (e.g., mutant dehalogenase) having a functional group (e.g., a green fluorophore, NANOLUC), then contacted with an agent and a substrate having a different functional group (e.g., an alternative fluorophore). In one embodiment, the mutant protein (e.g., mutant dehalogenase) is fused to a membrane localization signal and so can be employed to monitor events in or near the membrane.

In some embodiments, substrates and mutant proteins find use in the capture and/or identification of cellular targets of bioactive agents or drugs (e.g., peptides, small molecules, etc.) that interact therewith. Methods of such capture or identification are described, for example, in U.S. Ser. No. 61/736,426 and U.S. Ser. No. 61/736,429; herein incorporated by reference in their entireties.

The substrates and mutant proteins (e.g., dehalogenase) described herein are not limited to the above application. Substrates and mutant proteins (e.g., dehalogenase) may also find use in methods and applications described in, for example, U.S. Pat Pub. Nos.: 20120333001; 20120258470; 20120252048; 20120220013; 20120214677; 20110207195; 20110207195; 20110201024; 20110053162; 20110039257; 20110039257; 20110039257; 20100273186; 20090275051; 20090263843; 20090098627; 20090098627; 20090017482; 20080274488; 20080268482; 2008-145882; 20080090291;

Dexamethasone cadaverine adduct (10 mg, 21 umol) was combined with 2-(2-(2-(((4-nitrophenoxy)carbonyl)oxy) ethoxy)ethoxy)ethyl (2-(2-((6-chlorohexyl)oxy)ethoxy)ethylcarbamate (Hong et al., W. Am J Transl Res 2011, 3, 392; herein incorporated by reference in its entirety) (25 mg, 44 umol) and triethylamine in 2 mL DMF. After 2 h, the reaction was quenched by addition of 1 N HCl and the product was isolated by preparative HPLC eluting with 10→50% MeCN in aqueous 0.1% formic acid to yield 19 mg of a yellow solid. Calcd for $M+H(C_{44}H_{72}ClFN_3O_{12})$: 889. found 889.

Example 2

Experiments were conducted during development of embodiments of the present invention to demonstrate the efficiency of a pull-down (See schematic in FIG. 9) of a target protein from cells onto HALOTAG protein beads using carbamate chloroalkane drug conjugates. In this example, a BIRB-carbamate chloroalkane conjugate (PBI-4834; SEE FIG. 1) was utilized to pull down a NanoLuc-p38 alpha fusion protein from living cells.

HEK293 were plated and transfected using PEI with plasmid DNA encoding NANOLUC-p38 fusion in wells of a 96-well plate. Twenty-four hours post-transfection, cells were incubated with a final concentration of 10 μM PBI- 4834 while control cells were not treated with the conjugated drug. Following equilibration binding of 2 hours, the media was removed, and the cells were quickly washed with PBS and lysed in a detergent-based lysis buffer for 10 minutes. The cell lysates were then transferred to wells of a 96-well plate which contained 0.5 µl settled paramagnetic HALOTAG protein beads (obtained from Promega Corp.) and incubated with shaking for 15-45 minutes. Following binding, the unbound fraction was removed and the HALOTAG protein paramagnetic beads were washed. 150 uM unconjugated BIRB796 was then added and the captured NANOLUC-p38 alpha fusion was specifically released from the beads by competition with the unconjugated BIRB796 for 60 minutes. The released NANOLUC-p38 alpha fusion protein (+PBI-4834) and control (−PBI4834) was detected using NANOGLO luciferase reagent (Promega Corp.).

The high signal over background achieved within 15 minutes of capture on the HALOTAG protein beads demonstrates the efficiency of the capture method via the carbamate linker drug conjugate (FIG. 1).

Example 3

The following example demonstrates the advantages of the carbamate chloroalkane linker for cells permeability, binding affinity to a HaloTag® protein and target pull-down from cells onto HaloTag® beads via chloroalkane modified drugs. In this example, methotrexate-chloroalkane conjugates PBI-5015 (carbamate chloroalkane linker), PBI-4848 (O2 chloroalkane linker), PBI-4849 (O4 chloroalkane linker) and PBI-4850 (O6 chloroalkane linker) (SEE FIG. 2) were tested for their binding efficiency to HaloTag® protein in cells and in lysate.

a) Binding efficiency to HaloTag® protein in lysate was measured by adding the methotrexate-chloroalkane conjugates to lysate from cells expressing a HaloTag® protein to a final concentration of 1 µM. Following 0-60 mins of binding, the reactions were chased with 1 µM fluorescent HaloTag® ligand. Unbound HaloTag® protein was detected through binding to the fluorescent HaloTag® ligand followed by analysis on SDS-PAGE gel and detection on a fluorescent gel scanner.

Figure 3:
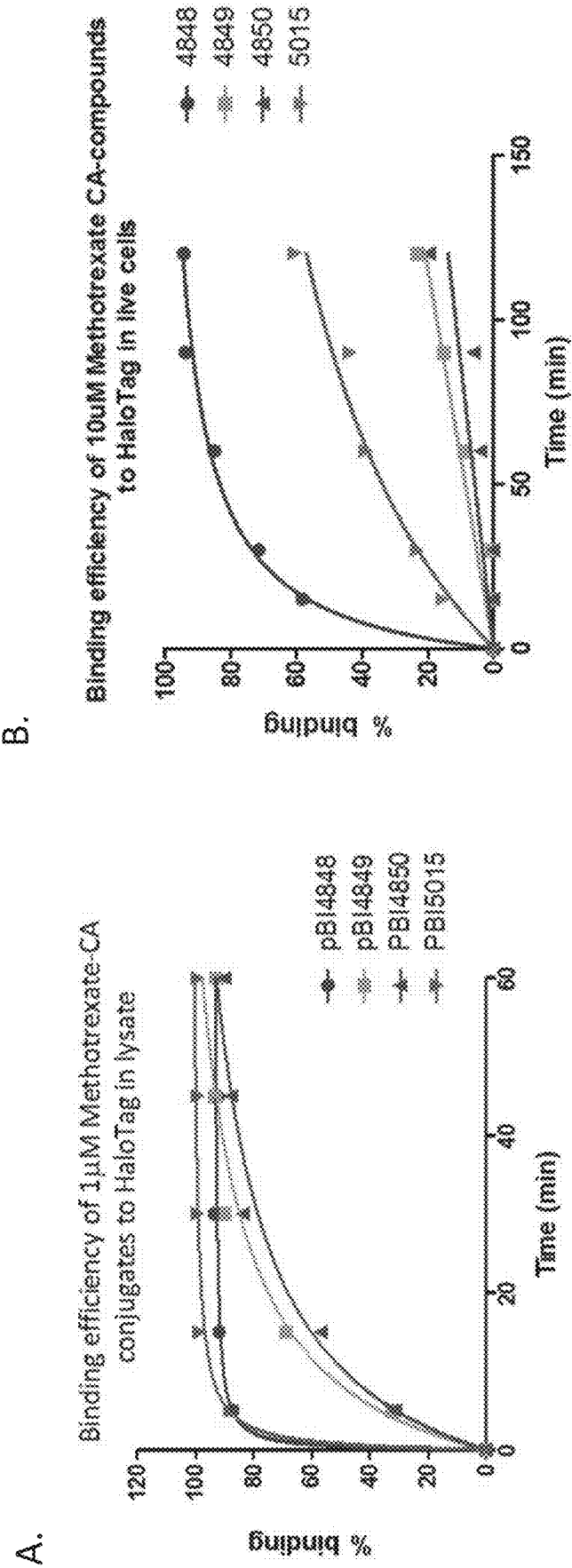
FIG. 3 shows the effect of linkers on the binding efficiency to a HaloTag® target protein from cell lysates (A) or cells (B) using chloroalkane-modified methotrexate substrates.

Results in FIG. 3A indicates that the $O_2$ linker (PBI-4848) and carbamate linker (PBI-5015) provided fast labeling kinetics to the HaloTag® protein compared to the other 2 linkers. The reduced binding efficiency of the O4 and O6 linkers can be attributed to their length. However, the length of the carbamate linker, which may be important for pull down applications didn't affect the binding efficiency to HaloTag.

b) Binding efficiency to HaloTag® protein in cells was measured by adding the methotrexate-chloroalkane conjugates to cells expressing a HaloTag® protein to a final concentration of 10 µM. Following 0-120 mins of binding, the reactions were chased with 5 µM fluorescent HaloTag® ligand. Unbound HaloTag® protein was detected through binding to the fluorescent HaloTag® ligand followed by cell lysis, analysis on a SDS-PAGE gel and detection on a fluorescent gel scanner.

Results in FIG. 3B indicates that the $O_2$ linker (PBI-4848) had the best cell permeability/binding efficiency to HaloTag® protein, followed by the carbamate linker (PBI-5015). The 2 other linkers O4 and O6 had significantly lower permeability/binding efficiency to HaloTag® protein. These results demonstrate that, although the carbamate linker is significantly longer than the O4 and O6, it still provides good cell permeability and binding efficiency to the HaloTag.

c) Based on the results above, the methotrexate-chloroalkane conjugates PBI-5015 (carbamate chloroalkane linker) and PBI-4848 (O2 chloroalkane linker), which provided the best cell permeability and binding efficiency to the HaloTag® protein, were tested for their ability to specifically pull-down a NanoLuc-DHFR fusion protein from living cells.

Figure 4:
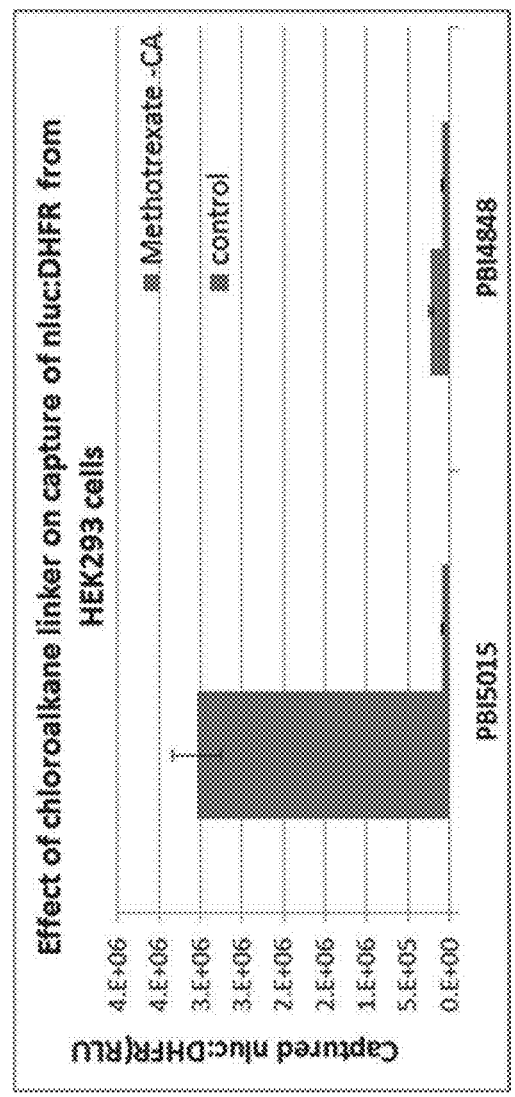
FIG. 4 shows a graph depicting the effect of linkers on the capture of a NanoLuc-DHFR fusion protein in cells.

HEK293 cells were plated and transfected using PEI with plasmid DNA encoding a NANOLUC-DHFR fusion in wells of a 96-well plate. The DNA was diluted 1:50 with a promoterless carrier DNA plasmid (pCI) to a final concentration of 80 ng total DNA per well. Twenty-four hours post-transfection, cells were serum starved for additional 24 hours and then treated with serially diluted with 10 uM PBI-4848 or PBI-5015 while control cells were not treated with the conjugated drug. Following equilibration binding of 2 h, the media was removed, and the cells quickly washed with PBS and lysed in detergent-based lysis buffer for 10 min. Cell lysates were then transferred to wells of a 96-well plate containing 0.5 µl settled paramagnetic HALOTAG protein beads and incubated with shaking for 45 min. Following binding, the unbound fraction was removed, the HALOTAG protein paramagnetic beads washed, 150 µM unconjugated methotrexate added, and the captured NANOLUC:DHFR specifically released from the beads by competition with the unconjugated methotrexate for 60 min. The released NANOLUC:DHFR (+PBI-5015 or +PBI-4848) and control samples were detected by NANOGLO luciferase detection reagent. Although both PBI-4848 and PBI-5015 have similar binding efficiency to HALOTAG protein, and PBI-4848 had higher cell permeability, only PBI-5015 efficiently pulled down the Nluc:DHFR fusion, thus demonstrating the advantage of the carbamate linker in pull-down applications (FIG. 4).

Example 4

Figure 5:
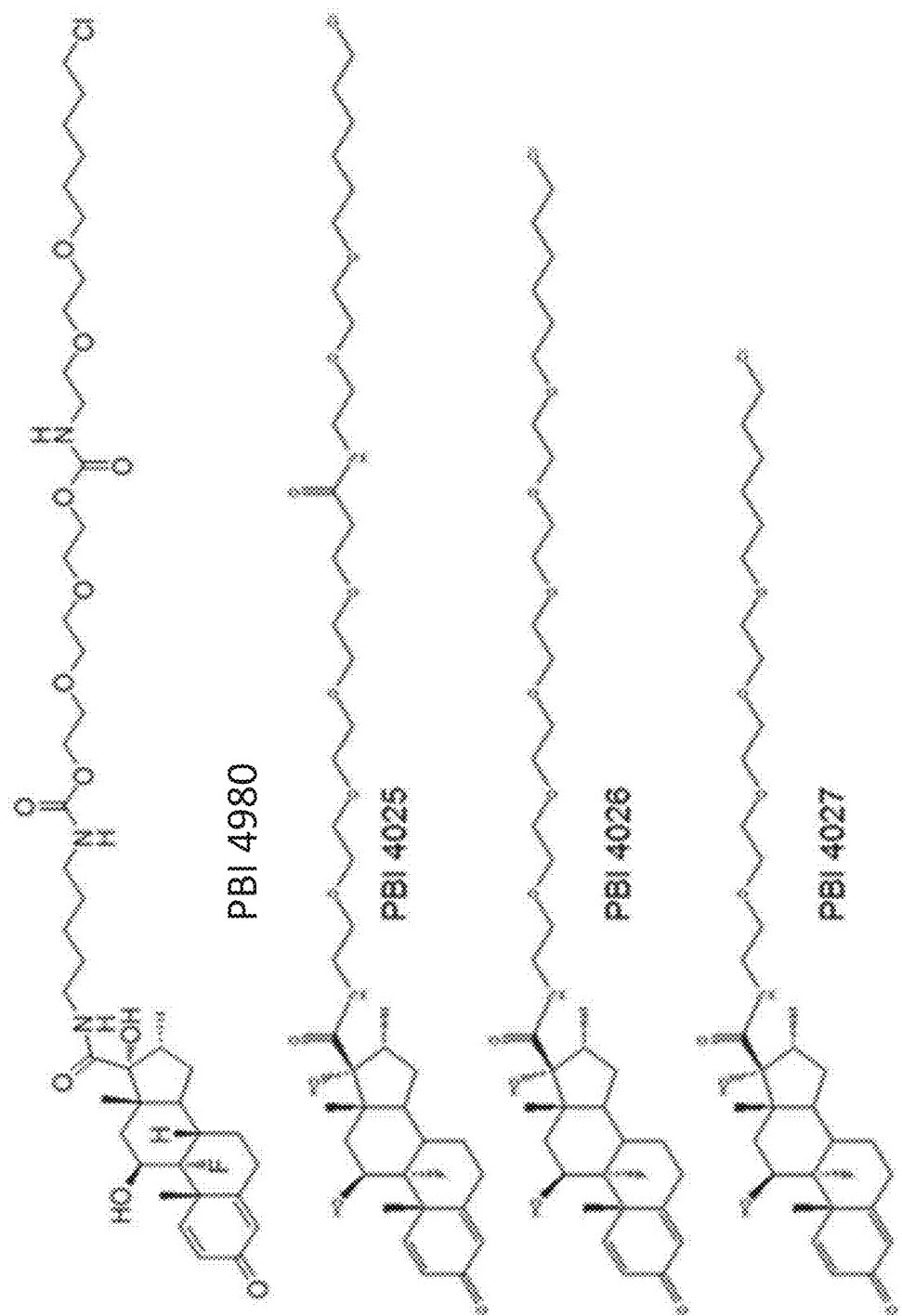
FIG. 5 provides structures of the substrates used in Example 4.

The following example demonstrates the advantage of the carbamate chloroalkane linker for cell permeability, binding affinity to HaloTag® protein, binding affinity to the target and target pull-down from cells onto HaloTag® beads via chloroalkane modified drugs. In this example, dexamethasone-chloroalkane conjugates PBI-4980 (carbamate chloroalkane linker), PBI-4027 (O2 chloroalkane linker), PBI-4026 (O4 chloroalkane linker) and PBI-4025 (O6 chloroalkane linker) (SEE FIG. 5) were tested for their binding efficiency to HaloTag® protein in cells and in lysates as well as their binding efficiency to the target, Glucocorticoid receptor.

a) Binding efficiency to HaloTag® protein in lysate was measured by adding the dexamethasone-chloroalkane conjugates to lysate from cells expressing a HaloTag® protein to a final concentration of 1 µM. Following 0-60 mins of binding, the reactions were chased with 1 µM fluorescent HaloTag® ligand. Unbound HaloTag® protein was detected through binding to the fluorescent HaloTag ligand followed by analysis on SDS-PAGE gel and detection on a fluorescent gel scanner.

Results in FIG. 6A indicate that the carbamate linker (PBI-4980) provided faster binding kinetics to the HaloTag® protein compared to the other 3 linkers demonstrating its advantage for rapid binding to HaloTag.

b) Binding efficiency to HaloTag® protein in cells was measured by adding the dexamethasone-chloroalkane conjugates to cells expressing a HaloTag® protein to a final concentration of 10 μM. Following 0-60 mins of binding, the reaction was chased with 5 μM fluorescent HaloTag ligand. Unbound HaloTag® protein was detected through binding to the fluorescent HaloTag® ligand followed by cell lysis, analysis on SDS-PAGE gel and detection on a fluorescent gel scanner.

Results in FIG. 6B indicate that the carbamate linker (PBI-4980) had the best cell permeability/binding efficiency to HaloTag® protein, followed by the O2 linker (PBI-4027) and the O4 linker and O6 linker, which had significant lower permeability/binding efficiency to HaloTag® protein. This result demonstrates that, although the carbamate linker is significantly longer than the O4 and O6, it still provides the best cell permeability and binding efficiency to the HaloTag.

c) Binding efficiency to the target glucocorticoid receptor (GR) was done using the glucocorticoid receptor competitor assay (Life Technology) as recommended by the manufacturer.

Figure 7:
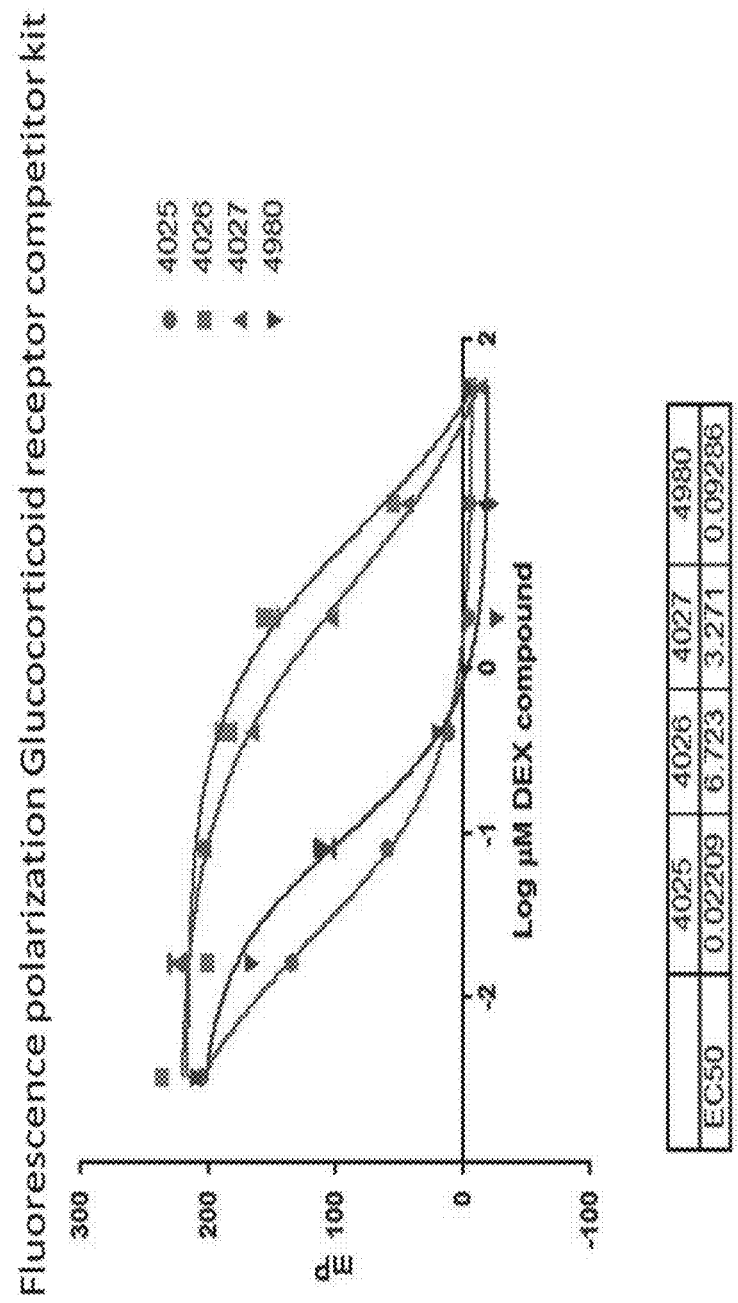
FIG. 7 shows a graph depicting the results of a fluorescence polarization assay of binding of dexamethasone to glucocorticoid receptor.

Results in FIG. 7 indicate that the longer linker O6 (PBI-4025) and the carbamate linker had the highest affinity to glucocorticoid receptor.

d) Based on the above results, the 2 linkers O6 (PBI-4025) and carbamate (PBI-4980), which provided the best binding efficiency to glucocorticoids receptor, were compared for their ability to specifically pull down NanoLuc:GR from live cells. HEK293 cells were plated and transfected using PEI with plasmid DNA encoding NanoLuc:GR fusion in wells of a 96-well plate. The DNA was diluted 1:50 with a promoter-less carrier DNA plasmid (pCI neo) to a final concentration of 80 ng total DNA per well. Twenty-four hours post-transfection, cells were serum starved for additional 24 hours then incubated with a final concentration of 10 μM PBI-4980 or PBI-4025 while control cells were not treated with the conjugated drug. Following equilibration binding of 2 h, the media was removed, cells quickly washed with PBS and lysed in detergent-based lysis buffer for 10 min. Cell lysates were than transferred to wells of a 96-well plate containing 0.5 μl settled paramagnetic HaloTag® protein beads and incubated with shaking for 45 min. Following binding the unbound fraction was removed, the HaloTag® protein paramagnetic beads were washed 3×, and the captured NanoLuc fusion was specifically released from the beads by competition with 150 μM unconjugated Dexamethasone for 60 min. The released NanoLuc:GR (+PBI-4980 or +PBI-4025) and control samples were detected by using the NanoGlo® assay reagent (Promega Corp).

Figure 8:
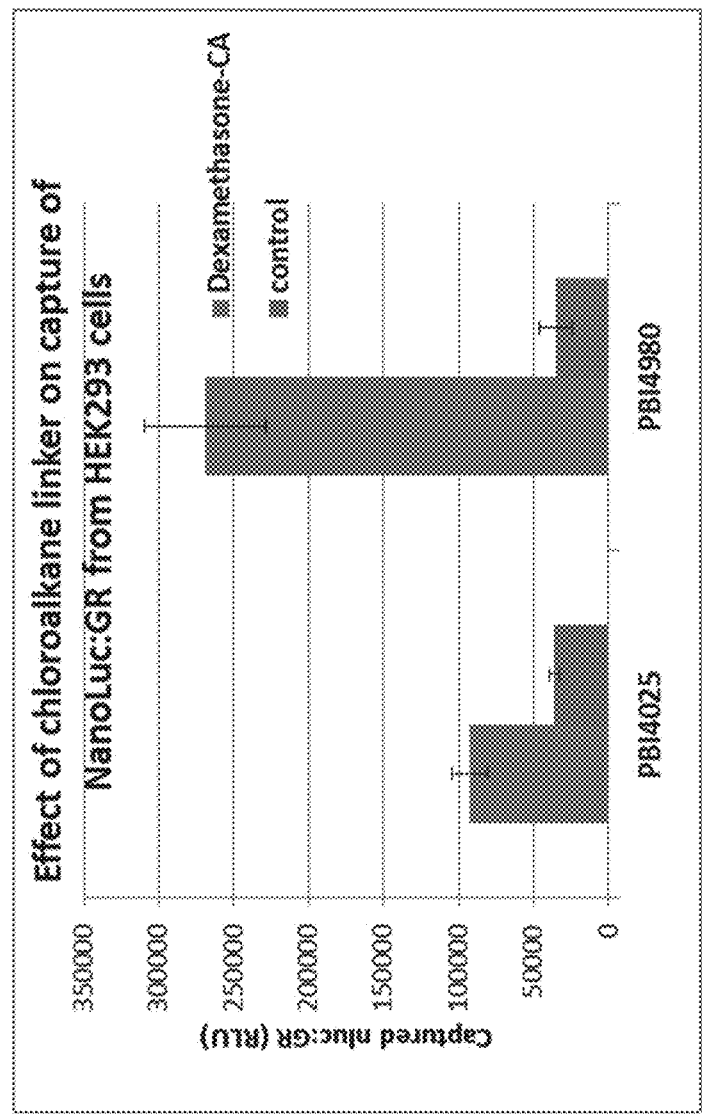
FIG. 8 shows a graph depicting the effect of the carbamate chloroalkane linker on the capture of a NanoLuc-GR fusion protein in cells.

Results in FIG. 8 indicate that although both linker have similar length, and PBI-4025 has higher affinity to glucocorticoid receptor, the efficiency of Nluc:GR fusion pull down via PBI-4980 (carbamate) was significantly higher than via PBI-4025, thus demonstrating the advantage of the carbamate linker in pull down applications. This efficient pull down is probably due to high binding efficiency of the carbamate linker to HaloTag® protein.

Example 5

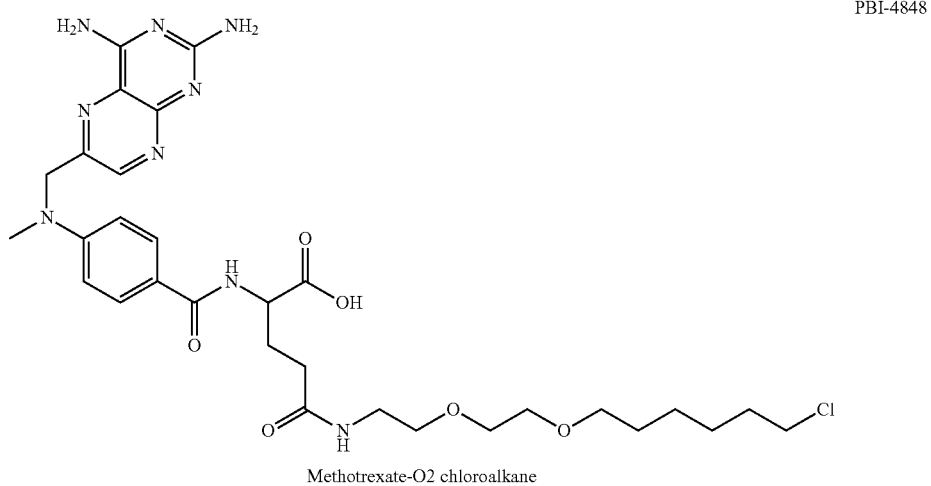 [SMILES: CN(Cc1cnc2nc(N)nc(N)c2n1)c1ccc(C(=O)NC(CCC(=O)NCCOCCOCCCCCCCl)C(=O)O)cc1]

Methotrexate-O2 chloroalkane 50 mg of methotrexate hydrate was stirred in 3 mL of DMF and treated with EDAC (63 mg, 330 umol) and triethylamine (77 uL, 550 umol). After 10 min, 2-(2-((6-chlorohexyl)oxy)ethoxy)ethylamine hydrochloride (Promega 21.5 mg, 83 umol) was added. After 3 h, the product was isolated by preparative HPLC (2→50% MeCN in 0.1% aqueous formic acid). The appropriate fractions were concentrated and lyophilized to yield an orange solid. Calcd for M+H: 660.3. found 660.7

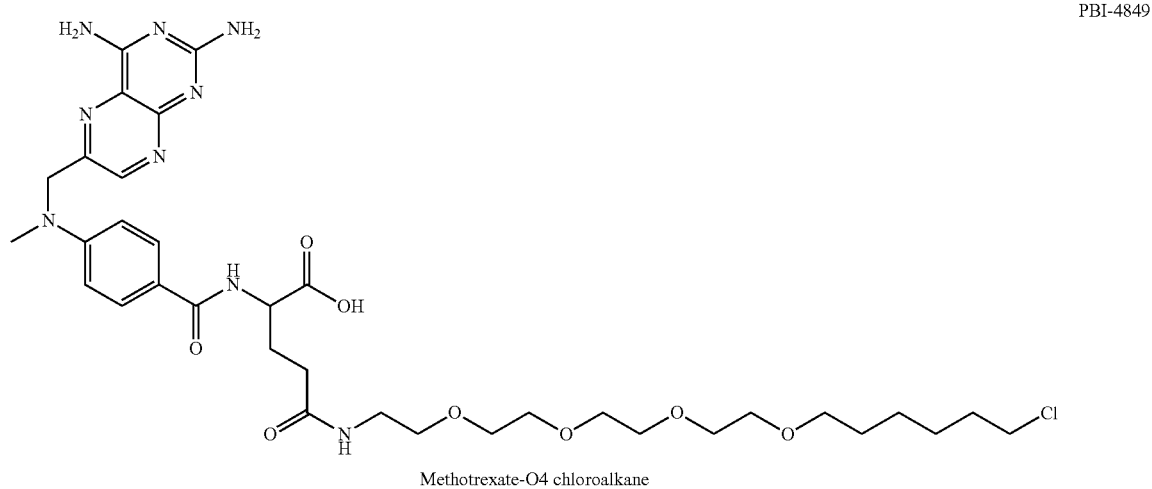 [SMILES: CN(Cc1cnc2nc(N)nc(N)c2n1)c1ccc(C(=O)NC(CCC(=O)NCCOCCOCCOCCOCCCCCCCl)C(=O)O)cc1]

Methotrexate-O4 chloroalkane

PBI 4849 was synthesized in a similar manner to PBI-4848 using 18-chloro-3,6,9,12-tetraoxaoctadecan-1-amine hydrochloride (Promega) to provide a yellow solid. Calcd for M+H: 749.3. found 748.9.

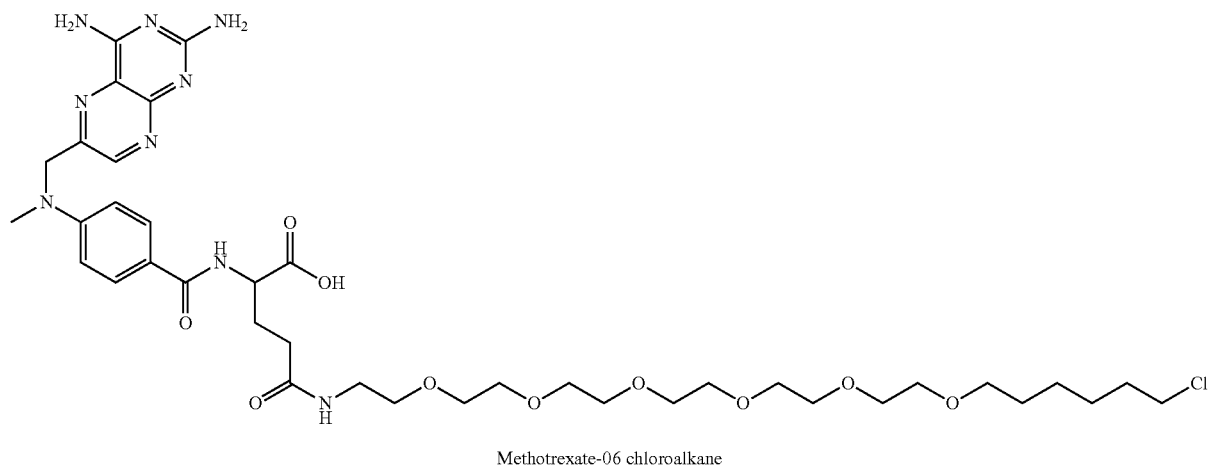

Methotrexate-O6 chloroalkane

PBI-4850 was synthesized in a similar manner to PBI-4848 using 24-chloro-3,6,9,12,15,18-hexaoxaoctadecan-1-amine hydrochloride (Benink et al.; BioTechniques 2009, 47, 769.; herein incorporated by reference in its entirety) to provide a yellow solid. Calcd for M+H: 837.4. found 837.4.
Methotrexate Pentylamine Intermediate To a mixture of methotrexate hydrate (50 mg, 110 umol), EDAC (63 mg, 330 umol) and triethylamine (77 uL, 550 umol) in 2 mL of DMF, N-Boc cadaverine (22 mg, 110 umol) was added. The reaction was stirred for 90 min, then quenched with 2 mL of 1 N HCl, diluted with water, and subjected to preparative HPLC (20→50% MeCN in 0.1% aqueous formic acid). The appropriate fractions were concentrated and lyophilized to yield the desired product. Calcd for M+H: 639.3. found 639.5.

Methotrexate N-Boc-cadaverine adduct (24 mg, 38 umol) was treated with 4 M HCl in dioxane (0.5 mL) at RT. Upon completion of the reaction, the solvents were removed under reduced pressure, and the resulting residue was stirred with diethyl ether to form a yellow precipitate which was isolated by centrifugation. The hydrochloride salt was used without further characterization.

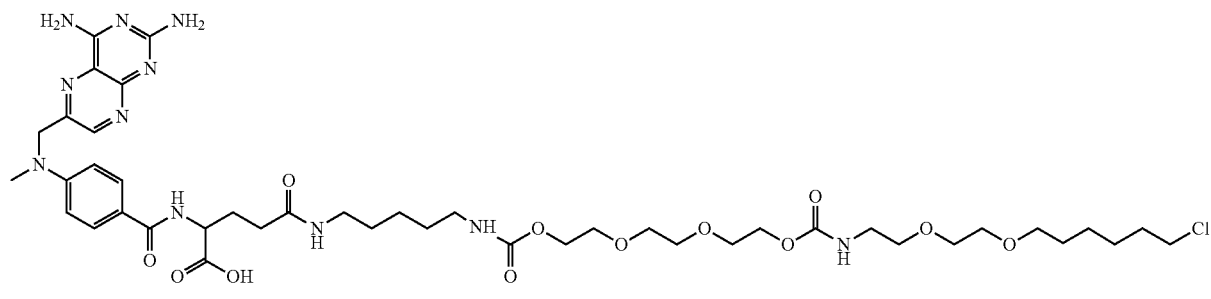

Methotrexate Carbamate Chloroalkane

Methotrexate hydrate pentylamine HCl salt (8 mg, 14 umol) was combined with 2-(2-(2-(((4-nitrophenoxy)carbonyl)oxy)ethoxy)ethoxy)ethyl (2-(2-((6-chlorohexyl)oxy)ethoxy)ethylcarbamate (Hong et al. Am J Transl Res 2011, 3, 392.; herein incorporated by reference in its entirety) (12 mg, 21 umol) and triethylamine in 2 mL DMF. After 2 h, the reaction was quenched by addition of 1 N HCl and the product was isolated by preparative HPLC eluting with 10→50% MeCN in aqueous 0.1% formic acid. After concentration, the resulting yellow solid was taken up in DCM and washed with saturated NaHCO$_3$. Evaporation of the organic layer yielded 1.9 mg of a yellow solid. Calcd for M+H: 964.5. found 964.5.

Example 6

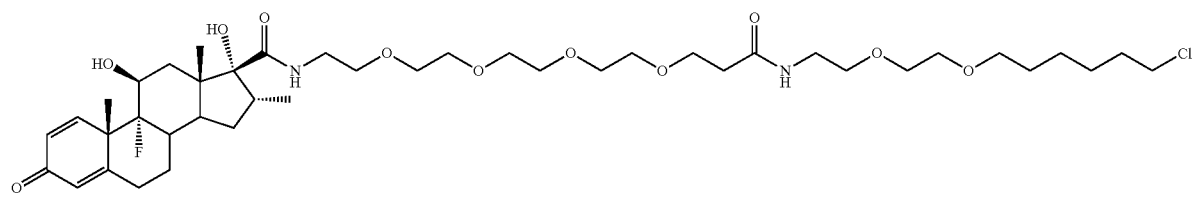

PBI-4025:

Dexamethasone acid (35 mg, 9.26×10$^{-5}$ mol) and PyBOP (53 mg, 0.1 mmol) were dissolved in 1 ml dry DMF. A 1 M solution of the HCl salt of 1-amino-N-(2-(2-((6-chlorohexyl)oxy)ethoxy)ethyl)-3,6,9,12-tetraoxapentadecan-15-amide (140 δl, 0.14 mmol) was added to the reaction mixture followed by five equivalence of diisopropylethylamine, DIPEA (62 δl, 0.37 mmol). The reaction was stirred for 3 hours whereupon volatile reagents were evaporated under vacuum. The residue was subjected to column chromatography using dichloromethane and methanol as eluent. A white solid was isolated (53 mg, 69%). MS (ESI) m/z calcd for $C_{42}H_{69}ClFN_2O_{11}^+$ (M$^+$H$^+$): 831.5. (found) 831.3.

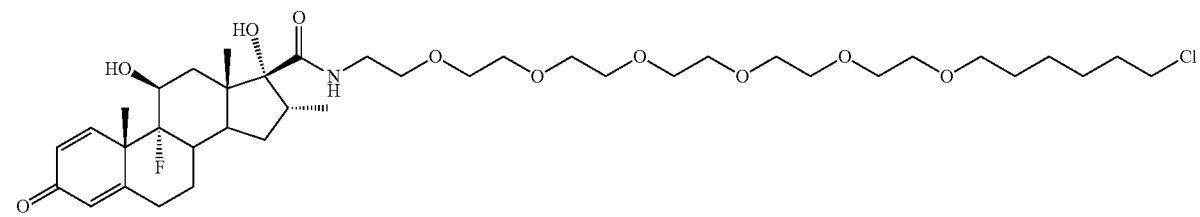

PBI-4026:

Dexamethasone acid (16 mg, 4.23×10$^{-5}$ mol) and PyBOP (24 mg, 4.65×10$^{-5}$ mol) were dissolved in 1 ml dry DMF. A 0.44 M solution of the HCl salt of 24-chloro-3,6,9,12,15,18-hexaoxatetracosan-1-amine (144 δl, 6.35×10$^{-5}$ mol) was added to the reaction mixture followed by four equivalence of DIPEA (24 δl, 0.17 mmol). The reaction was stirred for 3 hours whereupon volatile reagents were evaporated under vacuum. The residue was subjected to column chromatography using dichloromethane and methanol as eluent. A white solid was isolated (32 mg, quantitative). MS (ESI) m/z calcd for $C_{39}H_{64}ClFNO_{10}^+$ (M$^+$H$^+$): 760.4. (found) 760.3.

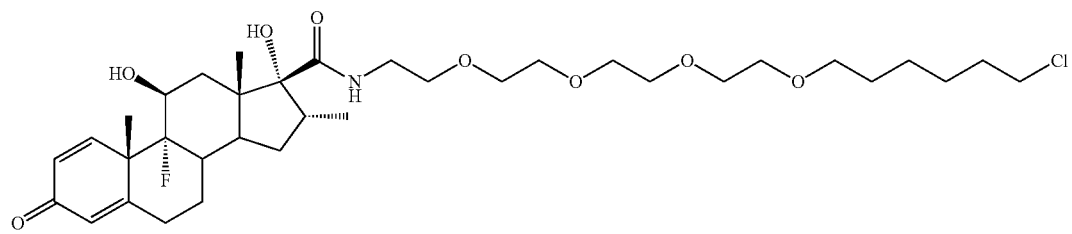

PBI 4027:

Dexamethasone acid (25 mg, 6.5×10$^{-5}$ mol), PyBOP (37 mg, 7.15×10$^{-5}$ mol) and 18-chloro-3,6,9,12-tetraoxaoctadecan-1-aminium chloride (34 mg, 9.76×10$^{-5}$ mol) were dissolved in 1 ml dry DMF. Four equivalence of DIPEA (45 δl, 0.26 mmol) was then added. The reaction was stirred for 3 hours whereupon volatile reagents were evaporated under vacuum. The residue was subjected to column chromatography using dichloromethane and methanol as eluent. A white solid was isolated (44 mg, quantitative). MS (ESI) m/z calcd for $C_{35}H_{56}ClFNO_{8}^+$ (M$^+$H$^+$): 672.4. (found) 672.4.

All publications and patents mentioned in the present application are herein incorporated by reference. Various modification, recombination, and variation of the described features and embodiments will be apparent to those skilled in the art without departing from the scope and spirit of the invention. Although specific embodiments have been described, it should be understood that the invention as claimed should not be unduly limited to such specific embodiments. Indeed, various modifications of the described modes and embodiments that are obvious to those skilled in the relevant fields are intended to be within the scope of the following claims.

The invention claimed is:

1. A cell permeable compound of formula R-L1-M-L2-A-X;
    wherein R is a functional group selected from an affinity tag, a fluorophore, a chromophore, a cross-linking group, an amino acid, a peptide, a polypeptide, a nucleotide, and a lipid; wherein R is not 1, 4, 7-triazacyclononane-N, N', N''-triacetic acid (NOTA);
    wherein M is a first carbamate group;
    wherein L1 is a first linker portion that comprises a second carbamate group; wherein the second carbamate group is separated from R by 2 or more linearly connected atoms; wherein the second carbamate group is separated from M by 2 or more linearly connected atoms;
    wherein L2 is a second linker portion;
    wherein A is $(CH_2)_6$; and X is a halogen; and
    wherein L2-A separates M and X by 6-18 linearly connected atoms.

2. The compound of claim 1, wherein L2-A separates M and X by 12 linearly connected atoms.

3. The compound of claim 1, wherein the functional group comprises an affinity tag or fluorophore.

4. The compound of claim 1, wherein L2 does not comprise a carbamate group.

5. The compound of claim 1, wherein L2 comprises linearly connected $CH_2$ and O groups.

6. The compound of claim 5, wherein L2 consists of linearly connected $CH_2$ and O groups.

7. The compound of claim 5, wherein L2 comprises $((CH_2)_2O)_x$, wherein x=0-5.

8. The compound of claim 7, wherein L2 comprises $((CH_2)_2O)_2$.

9. The compound of claim 1, wherein L1 comprises linearly connected $CH_2$ and O groups.

* * * * *